United States Patent
Beatty

(10) Patent No.: US 12,115,432 B2
(45) Date of Patent: Oct. 15, 2024

(54) INTERACTIVE INTELLIGENT SPORTS SYSTEM

(71) Applicant: Sloan Beatty, Birmingham, AL (US)

(72) Inventor: Sloan Beatty, Birmingham, AL (US)

( * ) Notice: Subject to any disclaimer, the term of this patent is extended or adjusted under 35 U.S.C. 154(b) by 270 days.

(21) Appl. No.: 17/633,831

(22) PCT Filed: Jul. 27, 2020

(86) PCT No.: PCT/US2020/043747
§ 371 (c)(1),
(2) Date: Feb. 8, 2022

(87) PCT Pub. No.: WO2021/021740
PCT Pub. Date: Feb. 4, 2021

(65) Prior Publication Data
US 2022/0296983 A1    Sep. 22, 2022

Related U.S. Application Data

(60) Provisional application No. 62/879,249, filed on Jul. 26, 2019.

(51) Int. Cl.
*A63B 71/06* (2006.01)
*A63B 24/00* (2006.01)
*A63B 102/32* (2015.01)

(52) U.S. Cl.
CPC ...... *A63B 71/0622* (2013.01); *A63B 24/0062* (2013.01); *A63B 2024/0015* (2013.01);
(Continued)

(58) Field of Classification Search
None
See application file for complete search history.

(56) References Cited

U.S. PATENT DOCUMENTS 9,154,739 B1 * 10/2015 Nicolaou ............... H04N 7/18
9,679,494 B2 *  6/2017 Ellis .................. A63B 24/0062
(Continued)

OTHER PUBLICATIONS

International Search Report and Written Opinion of the International Searching Authority for International Patent Application No. PCT/US2020/043747, dated Oct. 13, 2020, 15 pages.
(Continued)

*Primary Examiner* — Sunit Pandya
(74) *Attorney, Agent, or Firm* — DITTHAVONG, STEINER & MLOTKOWSKI

(57) ABSTRACT

An approach for providing real-time feedback during a sports activity (e.g., golf play) based, at least in part, on analysis of sensor information, is disclosed. The approach involves receiving sensor data associated with one or more sensors arranged to track playing technique information of a player engaged in a sports activity. The approach also involves processing the sensor data in real-time to determine the playing technique information. The approach further involves retrieving baseline information for the player. The approach also involves comparing the playing technique information with the baseline information. The approach further involves generating, in real-time with the engagement of the sports activity, an instructional message to modify playing technique of the player based on the comparison. The approach also involves initiating presentation, during the sports activity, of the instructional message to a user interface of a device accessible by the player.

18 Claims, 22 Drawing Sheets

(52) U.S. Cl.
CPC ......... *A63B 2024/0068* (2013.01); *A63B 2024/0096* (2013.01); *A63B 2071/0625* (2013.01); *A63B 2102/32* (2015.10); *A63B 2220/833* (2013.01); *A63B 2220/836* (2013.01)

(56) References Cited

U.S. PATENT DOCUMENTS

| | | | |
|---|---|---|---|
| 10,032,069 B2* | 7/2018 | Mizuochi | G06V 40/23 |
| 10,124,230 B2* | 11/2018 | Thornbrue | G06Q 10/0639 |
| 11,439,322 B2* | 9/2022 | Garay | A61B 5/7455 |
| 2010/0201512 A1* | 8/2010 | Stirling | A61B 5/11 |
| | | | 340/539.11 |
| 2012/0179278 A1 | 7/2012 | Riley et al. | |
| 2012/0212505 A1 | 8/2012 | Burroughs et al. | |
| 2013/0274904 A1 | 10/2013 | Coza et al. | |
| 2015/0131845 A1 | 5/2015 | Forouhar et al. | |
| 2016/0030834 A1 | 2/2016 | Brown et al. | |
| 2017/0072262 A1 | 3/2017 | Crowley et al. | |
| 2019/0183430 A1 | 6/2019 | Alphonse et al. | |

OTHER PUBLICATIONS

Mendes Jr. et al., "Sensor Fusion and Smart Sensor in Sports and Biomedical Application", Sep. 23, 2016, retrieved from https://www.ncbi.nlm.nih.gov/pmc/articles/PMC5087358/pdf/sensors-16-01569.pdf, 31 pages.

* cited by examiner

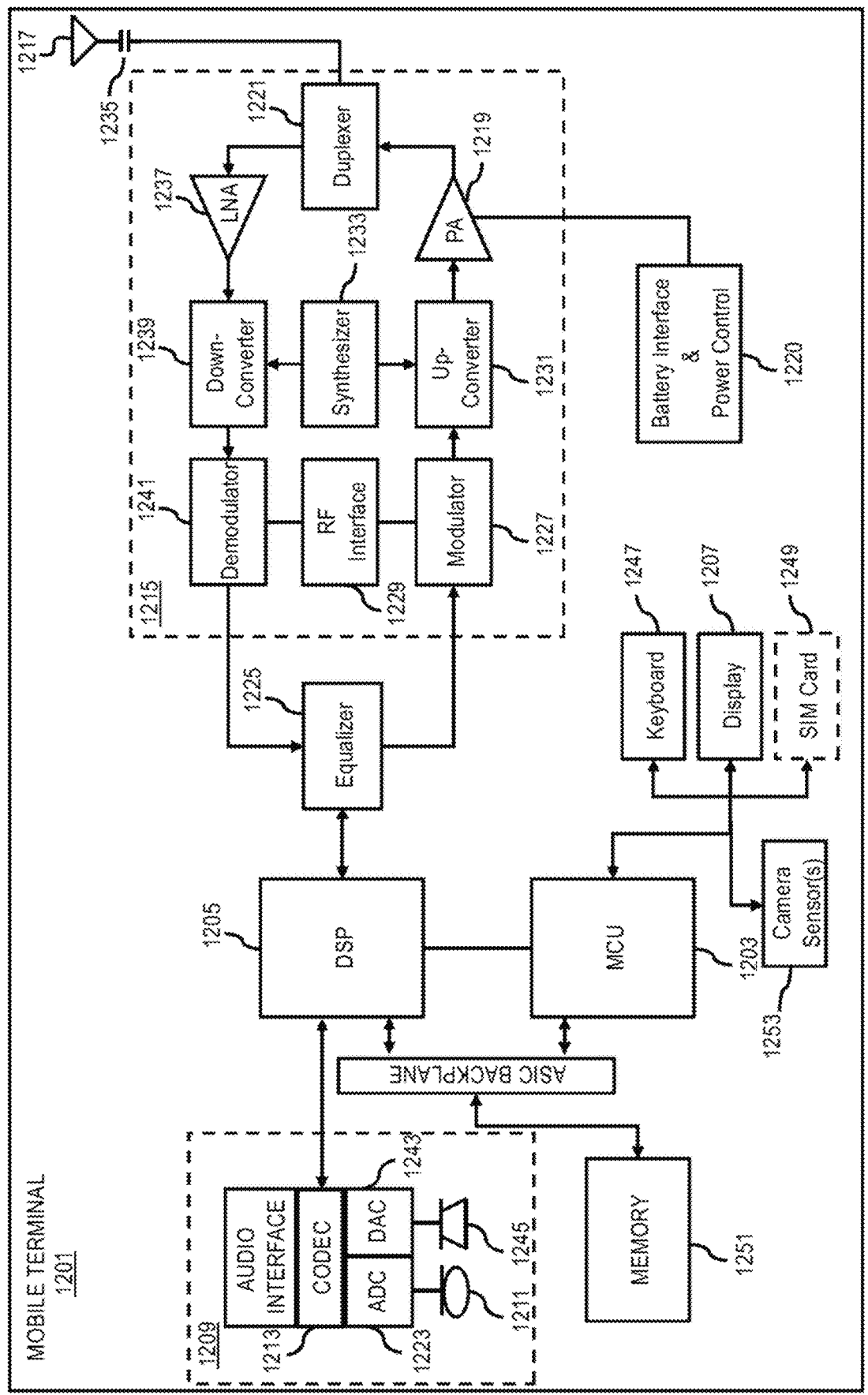

INTERACTIVE INTELLIGENT SPORTS SYSTEM

CROSS-REFERENCE TO RELATED APPLICATIONS

This application claims priority to U.S. Provisional Patent Application No. 62/879,249, filed on Jul. 26, 2019, the contents of which are hereby incorporated herein in their entirety by this reference.

BACKGROUND

The advances in social media, virtual reality, augmented reality, and sensor technologies (e.g., Internet of Things (IoT)) have impacted numerous industries, including sports. In particular, the golfing industry, for example, has experienced technological leaps in club design, swing analysis systems, gaming systems, instructional systems, simulations, etc. However, because of the disparate nature of the market segments and engineering efforts in these systems, an integrated approach has been lacking to better leverage these resources to maximize user experience. Other areas of sports (e.g., baseball, basketball, tennis, lacrosse, cricket, football, martial arts, etc.) similarly are deficient.

SOME EXAMPLE EMBODIMENTS

Therefore, there is a need for an integrated approach for providing real-time feedback while a user is engaged in a sports activity, e.g., playing golf, based, at least in part, on analysis of sensor data.

According to one embodiment, a method comprises receiving sensor data associated with one or more sensors arranged to track playing technique information of a player engaged in a sports activity. The method also comprises processing the sensor data in real-time to determine the playing technique information. The method further comprises retrieving baseline information for the player. The method also comprises comparing the playing technique information with the baseline information. The method further comprises generating, in real-time with the engagement of the sports activity, an instructional message to modify playing technique of the player based on the comparison. The method also comprises initiating presentation, during the sports activity, of the instructional message to a user interface of a device accessible by the player.

According to one embodiment, a system comprises one or more servers configured to receive sensor data associated with one or more sensors arranged to track playing technique information of a player engaged in a sports activity. The one or more servers are also configured to process the sensor data in real-time to determine the playing technique information. The one or more servers are further configured to retrieve baseline information for the player. The one or more servers are also configured to compare the playing technique information with the baseline information. The one or more servers are further configured to generate, in real-time with the engagement of the sports activity, an instructional message to modify playing technique of the player based on the comparison. The one or more servers are also configured to initiate presentation, during the sports activity, of the instructional message to a user interface of a device accessible by the player.

According to another embodiment, a non-transitory computer-readable storage medium carries one or more sequences of one or more instructions which, when executed by one or more processors, cause, at least in part, an apparatus to receive sensor data associated with one or more sensors arranged to track playing technique information of a player engaged in a sports activity. The apparatus is also caused to process the sensor data in real-time to determine the playing technique information. The apparatus is further caused to retrieve baseline information for the player. The apparatus is also caused to compare the playing technique information with the baseline information. The apparatus is further caused to generate, in real-time with the engagement of the sports activity, an instructional message to modify playing technique of the player based on the comparison. The apparatus is also caused to initiate presentation, during the sports activity, of the instructional message to a user interface of a device accessible by the player.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between the service provider and mobile device with actions being performed on both sides.

For various example embodiments, the following is applicable: An apparatus comprising means for performing a method of any of the claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIG. 12 is a diagram of a mobile terminal (e.g., handset) that can be used to implement various example embodiments.

DESCRIPTION OF SOME EMBODIMENTS

Examples of a method, apparatus, and computer program for providing real-time feedback during a golf play based, at least in part, on analysis of sensor information are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
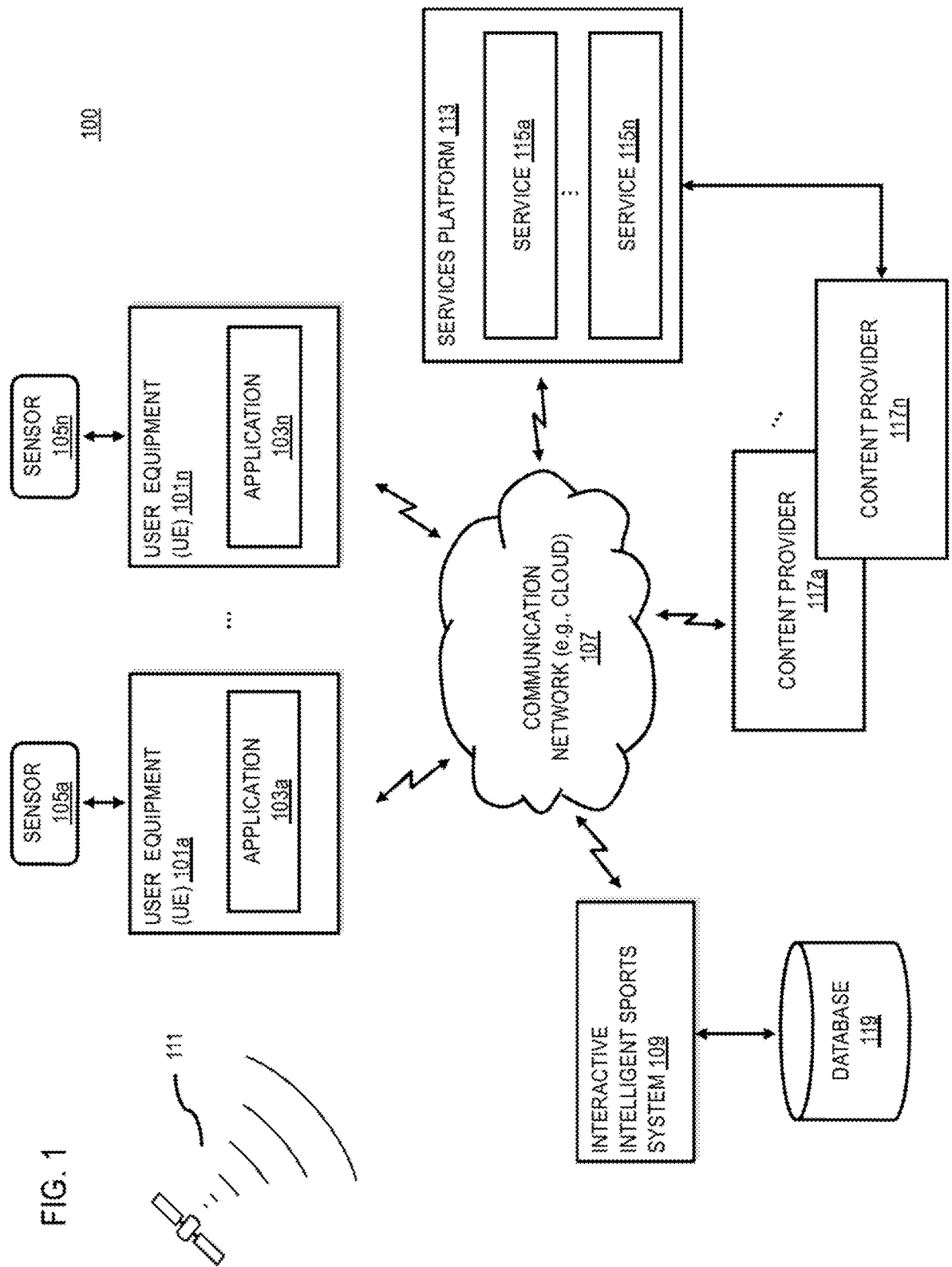
FIG. 1 is a diagram of an interactive intelligent sports system capable of providing real-time feedback during a sports activity based, at least in part, on analysis of sensor data from one or more sensors affixed to the player and/or equipment, according to one embodiment.

FIG. 1 is a diagram of an interactive intelligent sports system capable of providing real-time feedback during a sports activity based, at least in part, on analysis of sensor data from one or more sensors affixed to the player and/or equipment, according to one embodiment. Although the use cases described herein relate to golfing, it is contemplated that the processes and mechanisms of system 109 can be deployed to other sports, such as baseball, basketball, tennis, lacrosse, cricket, football, martial arts, etc. As noted, traditionally, the various tools and technologies within the sports industry (notably golf) lack integration. That is, valuable information that can be utilized to improve the players' skills and performance are not coordinated or accessible when needed. Golf swing analysis tools and applications can provide valuable information to the user, but not readily applied to a playing scenario. Additionally, golf instructions learned from a simulated environment or a coach cannot be easily recalled and adapted to real-world play. In a professional tournament, golfers may seek the help of a caddie to help understand and correct for these real-world conditions. Furthermore, because of the complexity of the game of golf, touring professionals (those with the means) are accompanied by their coaches to assist with making adjustments to the players' stance, position, swing, playing strategies, etc. With respect to recreational golfers, they may receive instructions from a golf pro at the facilities and perhaps use caddies. In effect, the knowledge base of the coaches and caddies about the player is not retained by the player, or can this knowledge be readily accessed.

Advancements in virtual reality and augmented reality have not infiltrated the golf instructional industry to any significant degree. This stems, in part, from not being able to maintain a real-time repository of instructional information, player information, and course information.

Another aspect of golf involves the simulation and video gaming industry. There has been little effort to create a gaming environment that can be instructional and entertaining, other than perhaps golf simulators. Golf simulators require physical space and are much more expensive than "video games."

To address the integration problem, a system 100 of FIG. 1 includes an interactive intelligent sports system 109 that introduces the capability to gather and store all information that can be used to provide real-time instructions to a user during play at a real golf course as well as "virtualize" the user into a video game as an avatar of the user. According to various embodiments, the system 109 collects sensor information from one or more sensors affixed to a user's headwear, apparel, golf club, shoe, and/or glove. This sensor information is collected in real-time as the user plays a game on a real golf course. Additionally, health information that can be collected in real-time via various sensors may be collected; such health information includes heart rate, blood pressure, muscle tension, rate of perspiration, etc. The collected information is transmitted to system 109 for real-time analysis. Depending on the level or degree of feedback/instructions desired, system 109 provides the appropriate feedback information to correct the player. In one embodiment, as compared to more detailed feedback, less detailed feedback entails the use of less sensor information, and thus, advantageously requires shorter processing time. Under this scenario, the system 109 can be more selective in processing only certain sensor information that is needed to produce the feedback. Additionally, depending on the user's selection of game mode, the virtualized play can reflect the actual play on the golf course; in this manner, the user can play against current players who are online, or past/recorded plays of other players (including the user's own past game). In another game mode, characteristics of the user (e.g., profile (likeness or true image; swing and playing style) are exported to play virtual courses as in a video game or simulator.

As shown in FIG. 1, the system 100 also comprises user equipment (UE) 101a-101n (collectively referred to as UE 101) that may include or be associated with applications 103a-103n (collectively referred to as applications 103) and sensors 105a-105n (collectively referred to as sensors 105). In one embodiment, the UE 101 has connectivity to the interactive intelligent sports system 109 via the communication network 107. In one embodiment, the interactive intelligent sports system 109 performs one or more functions associated with providing real-time feedback during golf play using collected sensor information.

By way of example, the UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, a smartphone, a smartwatch, smart eyewear, or any combination thereof, including the accessories and peripherals of these devices, or any combination thereof. It is also contemplated that the UE 101 can support any type of interface to the user (such as "wearable" circuitry, etc.). In one embodiment, the UE 101 may include Global Positioning System (GPS) receivers to obtain geographic coordinates from satellites 111 for determining current location and time associated with the UE 101.

By way of example, the applications 103 may be any type of application that is executable at UE 101, such as content provisioning services, camera/imaging application, media player applications, social networking applications, calendar applications, and the like. In one embodiment, the applications 103 may assist in conveying sensor information via the communication network 107. In another embodiment, one of the applications 103 at the UE 101 may act as a client for the interactive intelligent sports system 109 and perform one or more functions associated with the functions of the interactive intelligent sports system 109 by interacting with the interactive intelligent sports system 109 over the communication network 107.

By way of example, the sensors 105 may be any type of sensor that measures conditions of the player and/or the environment experienced by the player with the purpose of gaining information that may impact the player's performance. In certain embodiments, the sensors 105 may include, for example, oriental sensors augmented with height sensor and acceleration sensor, tactile sensors, tilt sensors, pressure sensors, gaze tracking sensors, electromagnetic sensors, e.g., radiofrequency sensors or ultrasound sensors, proximity sensor, a global positioning sensor for gathering location data, a network detection sensor for detecting wireless signals or receivers for different short-range communications (e.g., Bluetooth, Wi-Fi, Li-Fi, near field communication (NFC) etc.), temporal information sensors, a camera/imaging sensor for gathering image data, an audio recorder for gathering audio data, light sensors, and the like. In one scenario, sensors 105 may track the gaze of one or more users using one or more cameras and/or gaze tracking sensors affixed to the player and/or equipment that is directed at the user's eyes. In another scenario, sensors 105 may detect the degree/angle of a golf club swing using one or more tilt sensors attached to the player and/or equipment. In a further scenario, sensors 105 may measure the acceleration of the golf club using a plurality of acceleration sensors, electromagnetic sensors, and/or ultrasound sensors embedded and/or affixed to the shaft or head of a golf club. In another scenario, sensors 105 may determine hand position and measure a player's grip using tactile sensors, pressure sensors, respectively, embedded and/or affixed to a golf club. It is contemplated that the UE 101 may itself contain sensors (e.g., camera) to capture images and environmental conditions, e.g., lighting and wind (if image analysis yields that clothing, towel, flag, trees, etc. are in motion).

The communication network 107 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short-range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including 5G ($5^{th}$ Generation), 4G, 3G, 2G, Long Term Evolution (LTE), enhanced data rates for global evolution (EDGE), general packet radio service (GPRS), global system for mobile communications (GSM), Internet protocol multimedia subsystem (IMS), universal mobile telecommunications system (UNITS), etc., as well as any other suitable wireless medium, e.g., worldwide interoperability for microwave access (WiMAX), code division multiple access (CDMA), wideband code division multiple access (WCDMA), wireless fidelity (Wi-Fi), wireless LAN (WLAN), Bluetooth®, Internet Protocol (IP) data casting, satellite, mobile ad-hoc network (MANET), and the like, or any combination thereof.

In one embodiment, the interactive intelligent sports system 109 may be a platform with multiple interconnected components. The interactive intelligent sports system 109 may include multiple servers, intelligent networking devices, computing devices, components, and corresponding software for providing real-time feedback to a player engaged in a sports activity (e.g., golf) based, at least in part, on analysis of sensor information. In addition, it is noted that the interactive intelligent sports system 109 may be integrated or separated from services platform 113. Also, certain functionalities of the system 109 may reside within the UE 101 (e.g., as part of the applications 103).

In one embodiment, the interactive intelligent sports system 109 receives sensor data from one or more sensors embedded and/or attached to one or more apparatuses. The sensor data can be associated with a playing technique or tendencies of an individual player during a golf play, e.g., stance, position, swing, playing strategies, etc. The interactive intelligent sports system 109 processes the sensor data in real-time to determine whether the playing technique of the individual player meets a predetermined threshold level. In one embodiment, the interactive intelligent sports system 109 may compare the swing of registered players to the swing of the professional player. In one embodiment, a playing technique does not satisfy a predetermined threshold level if the player bends his/her wrist beyond a prescribed limit. In another example embodiment, the playing technique does not satisfy a predetermined threshold level if the player swings the golf club beyond a recommended range. In a further example embodiment, the threshold is not satisfied if the user exerts excessive gripping pressure, i.e., an improper golf grip, during a swing.

Thereafter, the interactive intelligent sports system 109 generates, in real-time, one or more recommendations to improve the playing technique of the individual player based, at least in part, on a determination that the predetermined threshold level has not been satisfied. The interactive intelligent sports system 109 presents, in real-time, one or more recommendations/instructions (i.e., instructional messages) via at least one user interface of at least one UE 101 during the golf play. In another embodiment, the interactive intelligent sports system 109 may transmit swing data of a particular player to a registered coach based, at least in part, on a determination that the swing data of player does not satisfy a predetermined threshold level.

In another embodiment, the interactive intelligent sports system 109 collects data from an apparatus (e.g., smartphone) embedded with a plurality of sensors and/or standalone sensors affixed to any combination of shoes, socks, glove, watch, wrist band/device, armband, shirt, or cap. Such standalone sensors may utilize near field communication (NFC) technology, e.g., Bluetooth, to connect to a mobile device, e.g., smartphone, to send sensor data to cloud storage; this information then undergoes real-time analysis by the system 109 to generate feedback for the user/player. The real-time analysis, in certain embodiments, involves evaluating a user's movement, e.g., swing movement, golf characteristics, e.g., posture, and any other parameters associated with playing golf. Furthermore, the system 109 may utilize the sensors data in a virtual reality environment that is accessible via various devices, e.g., smart devices, video games, etc., for feedback or gaming purposes. In addition, user profile information, preference information, images, etc., may be exported to a video game or simulator.

In one embodiment, the interactive intelligent sports system 109 may compare the swing of a registered player (e.g., amateur golfer) with the swing of another player (e.g., professional golfer) to generate feedback information. In another example embodiment, the interactive intelligent sports system 109 may transmit sensor data of the user to a coach for analysis to obtain direct feedback from the coach. In other words, the coach is available to analyze the player from a physically different geographic location to review processed information derived from the sensor data; such processed information may be the player's posture, swing speed, swing angles, etc. In addition to or supplemental to the coach, the interactive intelligent sports system 109 can act as a "virtual" coach by using an Artificial Intelligence (AI) engine to simulate the coaching style of the human coach in evaluating the player's golf movements and environmental conditions. Furthermore, the system 109 may generate various reports from the user's sensor data to provide periodic reports (along with pertinent images, if captured during play) on the player's performance. In this manner, the coach can review all such reports "off-line" to work with the player after the actual golf play is over. In one example embodiment, the interactive intelligent sports system 109 compares, in real-time, a player's swing to a pre-recorded swing, which can serve as a baseline. Such baseline can be based on various criteria (e.g., latest swing, best swing, good swing in similar environmental conditions, etc.). The interactive intelligent sports system 109 may determine that the player's swing does not meet a predetermined threshold or a set of criteria, e.g., the player swings the golf club beyond a recommended range prescribed during the lesson. Thereafter, the interactive intelligent sports system 109 generates, in real-time, live coaching to improve the swing technique of the player. The interactive intelligent sports system 109 may select, in real-time, a pre-recorded coaching feedback for the situation. The selection of pre-recorded coaching is based, at least in part, on sensor data received from one or more sensors 105.

The system 109 can take advantage of the fact that the real-time analysis may be optimized depending on the level or degree of feedback/instructions desired. In one embodiment, the interactive intelligent sports system 109 determines that a player requires less detailed feedback (e.g., as specified by the user from the application 103 running on the UE 101). Consequently, the interactive intelligent sports system 109 can reduce the processing time of the sensor data to generate instructions to the player.

As shown in FIG. 1, the system 109 can interface a services platform 113, which provides various services, such as notification services, content (e.g., audio, video, images, etc.) provisioning services, application services, storage services, contextual information determination services, social networking services, location-based services, information-based services, etc. In one embodiment, the services platform 113 may interact with the UE 101, the interactive intelligent sports system 109, and the content provider 117 to supplement or aid in the processing of the content information.

By way of example, the services 115 may be an online service that reflects the interests and/or activities of users. Such activities may include other physical activities associated with other sports or events. The services 115 allow users to share activities information, contextual information, historical user information, and interests within their individual networks and provides for data portability. In this way, the platform provides the interactive intelligent sports system 109 with activity information for at least one user, user profile information, and a variety of additional information, and a variety of additional information to avoid redundancy data capture as well as possibly enhance the analysis for the player. For example, if the user were involved with physical activity (e.g., tennis match, social event that resulted in lack of rest, etc.) that may affect the user's performance and thus the user's golf swing, the system 109 may take this into account.

In the embodiment of FIG. 1, content providers 117a-117n (collectively referred to as content provider 117) may provide content to the UE 101, the interactive intelligent sports system 109, and the services 115 of the services platform 113. The content provided may be any type of content, such as image content (e.g., pictures), textual content, audio content, video content, etc. In one embodiment, the content provider 117 may provide content that may supplement the content of the applications 103, the sensors 105, or a combination thereof. In another embodiment, the content provider 117 may also store content associated with the UE 101, the interactive intelligent sports system 109, and the services 115 of the services platform 113. In a further embodiment, the content provider 117 may manage access to a central repository of data and offer a consistent, standard interface to data.

Associated with the interactive intelligent sports system 109 is database 119. It is contemplated that database 119 can be implemented as a cloud storage system. In one embodiment, the database 119 stores sensor data as well as profile information, e.g., player profiles, coach profiles, of one or more registered users. In another embodiment, the database 119 stores performance data for rounds of golf played by one or more registered players. In a further embodiment, the database 119 stores conditions and standards pertaining to playing technique for a golf play.

By way of example, UE 101, the interactive intelligent sports system 109, the services platform 113, and the content provider 117 communicate with each other and other components of the communication network 107 using well known, new or still developing protocols (e.g., IoT standards and protocols). In this context, a protocol includes a set of rules defining how the network nodes within the communication network 107 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
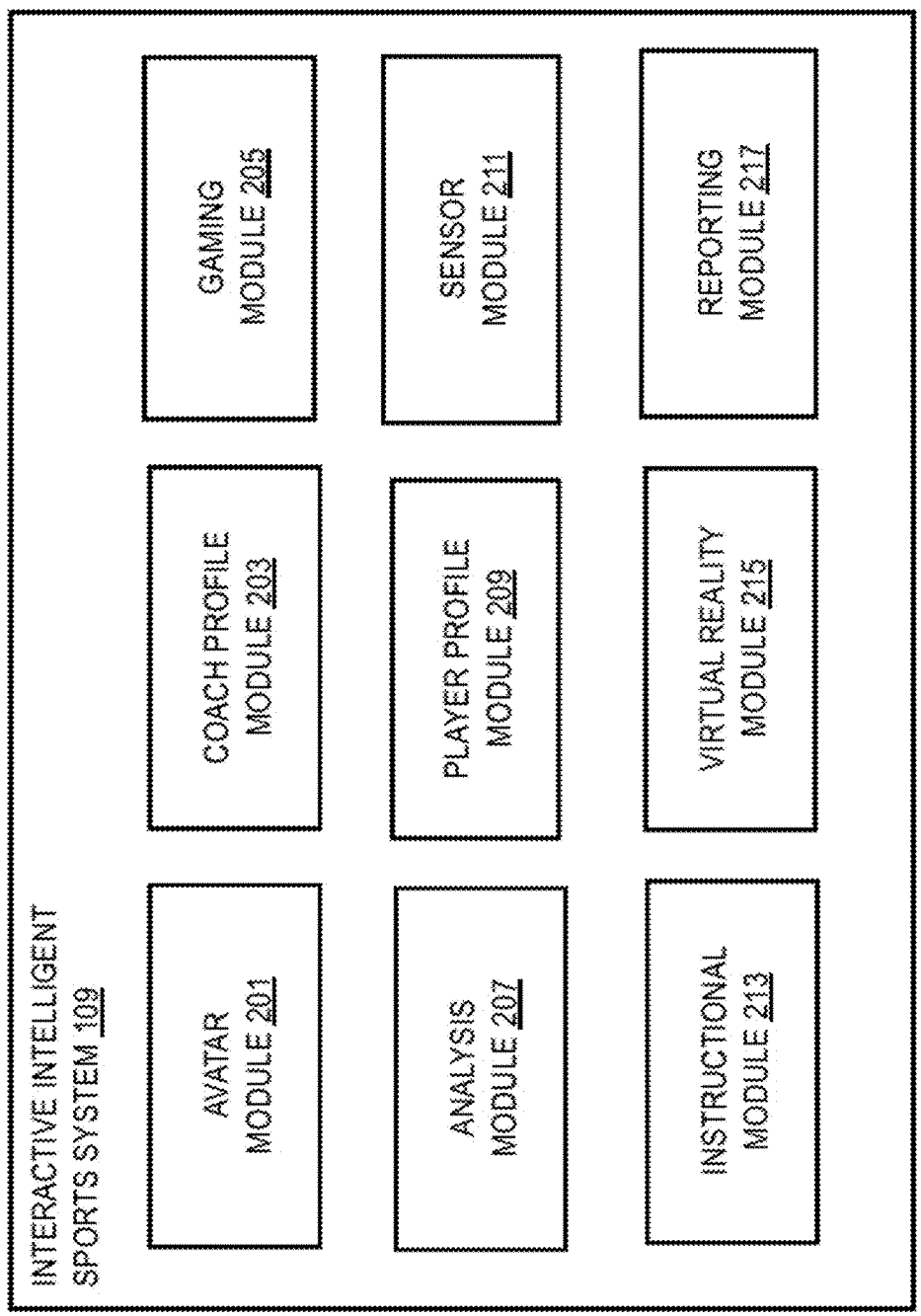
FIG. 2 is a diagram of the components of the interactive intelligent sports system of FIG. 1, according to one embodiment.

FIG. 2 is a diagram of the components of the interactive intelligent sports system 109, according to one embodiment. By way of example, the interactive intelligent sports system 109 includes one or more components for providing real-time feedback during a golf play based, at least in part, on analysis of sensor information. It is contemplated that the functions of these components may be combined in one or more components or performed by other components of equivalent functionality. In this embodiment, the interactive intelligent sports system 109 includes an avatar module 201, a coach profile module 203, a gaming module 205, an analysis module 207, a player profile module 209, a sensor module 211, an instructional module 213, a virtual reality module 215, and a reporting module 217.

In one embodiment, the avatar module 201 creates, manages, and stores data pertaining to players to represent them in a virtual environment (e.g., video game). An avatar may be any representation or manifestation including but not limited to a static or animated picture of a user, or a graphical object that may represent the user's movements, appearance, identity, and the like. As such, the avatar assumes playing characteristics (e.g., playing technique) of the user as well as health (e.g., based on collected health and medical information) and physical traits. The avatar module 201 allows a user to select a pre-designed avatar representative of themselves. In another embodiment, the user may further customize or otherwise alter the pre-designed avatar, e.g., color scheme, apparels, and the like, to generate a more desirable representation of themselves.

In one embodiment, the coach profile module 203 maintains a profile, e.g., description and attribute information, for each coach registered with the system 109. For example, when a coach initially creates an account with the system 109, the coach may be presented with a questionnaire requesting the coach to indicate specialties, certifications, background, and other relevant information that may be useful for a potential client or player. The answers to the questionnaire are used to generate a coach profile by the coach profile module 203. Additionally, using the answers to the questionnaire, the coach profile module 203 may dynamically rank coaches for presentation to a player seeking a coach, based on the player's stated goals in their profile or survey. The ranking may also take into consideration feedback from other users regarding each coach's engagement with users, behavior towards the users, and results of the users employing the particular coach.

According to certain embodiments, the gaming module 205 can interface various gaming systems to provide the player's avatar and the player's golfing characteristics. As such, the gaming module 205 in conjunction with the virtual reality module 215 allows a user to "virtualize" the user's actual real-world golf play into a corresponding virtual game. The gaming module 205 can update the player position and gameplay in the virtual world based on the actual position and play of the player in the real-world. For example, as the player moves around in the real-world, the sensors 105 tracks the position of the player and provides the player position information to the gaming module 205. In particular, the location of the player in the virtual world can correspond to the location of the player in the real-world.

Accordingly, the user's performance in the real-world golf course can be replicated in a virtual environment representing real-world golf courses; in this manner, other gamers who are not on the real golf course can play along as well as other players who are playing the real golf course.

As seen in FIG. 2, the system 109 includes analysis module 207, which analyzes sensor information received from of the various sensors attached to a player or embedded in a golf club to determine whether the playing technique of the player satisfies a predetermined threshold level or acceptable profile. In one embodiment, the analysis module 207 performs a swing analysis by detecting and determining various strokes of the player and may recommend swing adjustment based on the analysis. In another embodiment, the analysis module 207 performs a posture analysis by detecting the posture of the player and may recommend posture adjustment based on the analysis.

In one embodiment, the player profile module 209 maintains a profile for each user, i.e., player, registered with the system 109. In one embodiment, when a player initially creates an account with the golf analysis system, the player may be presented with a questionnaire requesting the player to indicate personal data, personal goals, weak area, and other information that may be useful for a potential coach to know about the player. These answers to the questionnaire are used to generate a player profile by the player profile module 209. In another embodiment, the player profile module 209 tracks player performance, gather skill ratings, generate composite scores, and provide data analytics to aid coaches and/or instructors in managing and developing players. In a further embodiment, the player profile module 209 provides a player assessment as compared to other players and indicate opportunities for player improvement.

In one embodiment, the sensor module 211 provides the software interface and protocols (e.g., Internet of Things (IoT) standards) to receive sensor data from the various sensors and transmit the sensor information to one or more modules for processing.

In one embodiment, the instructional module 213 provides aural or visual instructions regarding the playing technique, e.g., swing motion, of a player. For instance, the feedback may comprise of a synthesized or pre-recorded audio or video instructions that can be presented to the user via the UE 101 or other devices, such as a smartwatch or wrist device with a display and/or speaker. The instructional module 213 interacts with other modules, e.g., analysis module 207, to generate such feedback based on the swing characteristics of the player. In one embodiment, the instructional module 213 can obtain coaching style information from the coach profile module 23 to provide appropriate instruction. This coaching style information can be acquired by input from the coaches; system 109 can be trained to provide their teaching methods via AI, for instance. Additionally, the instructional module 213 can compare and correlate the various feedback given to the golfer/player, so as to determine the effectiveness of each feedback to the golfer/player. The instructional module 213 can use this determination in selecting appropriate future feedback for the golfer/player. In this manner, the feedback generated by the analysis module 207 can be prioritized, with the feedback that is determined to be generally ineffective being assigned a lower priority or being eliminated from consideration.

In one embodiment, the virtual reality module 215 obtains sensor data and scale live video for display by a virtual reality device, e.g., UE 101, based on the sensor data. Virtual reality can be a three-dimensional computer-generated interface that allows users to see, "move through" and interact with information displayed as a three-dimensional world. In one embodiment, a live television display area may be defined within graphics of a virtual reality program or application executed by the virtual reality device. The field-of-view and viewing angle of a virtual reality 3D environment may change based on the sensor data. In one embodiment, the virtual reality module 215 interacts with the gaming module 205 to allow a user to navigate through a virtual reality world as part of a golf video game.

In one embodiment, the reporting module 217 accesses data and metrics of individual users (e.g., players and coaches) to generate relevant reports for the interactive intelligent sports system 109. Subsequently, the reporting module 217 can provide the reports in real-time to the registered users, e.g., players, coaches.

The above-presented modules and components of the interactive intelligent sports system 109 can be implemented in hardware, firmware, software, or a combination thereof. Though depicted as a separate entity in FIG. 1, it is contemplated that the interactive intelligent sports system 109 may be implemented for direct operation by respective UE 101. As such, the interactive intelligent sports system 109 may generate direct signal inputs by way of the operating system of the UE 101 for interacting with the applications 103. In another embodiment, one or more of the modules 201-217 may be implemented for operation by respective UEs, the interactive intelligent sports system 109, or combination thereof. Still further, the interactive intelligent sports system 109 may be integrated for direct operation with services 115, such as in the form of a widget or applet, in accordance with an information and/or subscriber sharing arrangement. The various executions presented herein contemplate any and all arrangements and models.

Figure 3A:
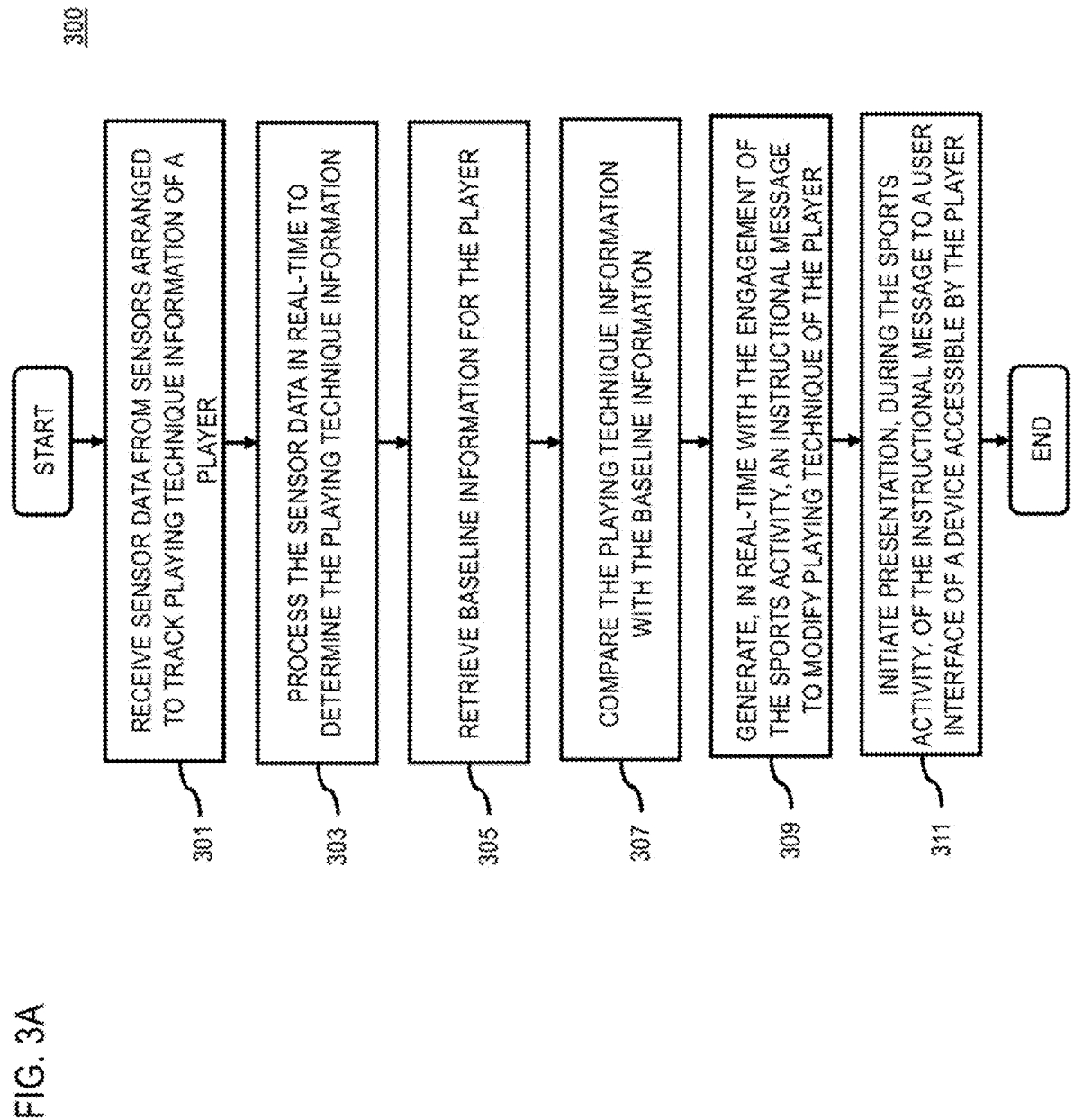
FIG. 3A is a flowchart of a process for providing real-time feedback during a sports activity, according to one embodiment.
Figure 11:
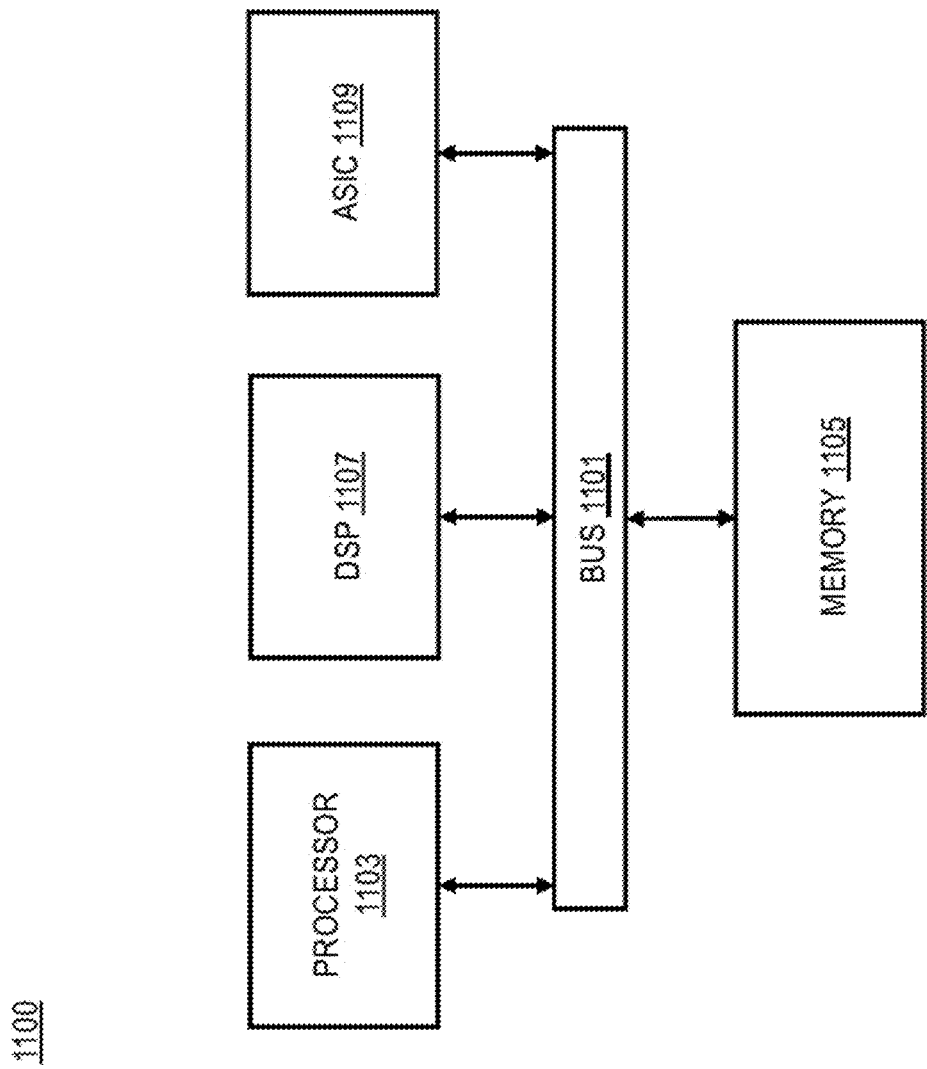
FIG. 11 is a diagram of a chip set that can be used to implement various example embodiments.

FIG. 3A is a flowchart of a process for providing real-time feedback during a sports activity, according to one embodiment. In one embodiment, the interactive intelligent sports system 109 performs the process 300 and is implemented in, for instance, a chip set including a processor and a memory as shown in FIG. 11.

In step 301, the interactive intelligent sports system 109 receives sensor data associated with one or more sensors arranged to track playing technique information of a player engaged in a sports activity, such as golf play on a real golf course. In one embodiment, the one or more sensors are embedded or attached to apparatuses, apparels, wrist bands, or a combination thereof of the player to track the playing technique. In one example embodiment, the player may launch a golf application 103 resident on UE 101 to interact with the system 109 and to request real-time playing instructions while playing golf at a real golf course; the application 103 enters into a real-time instruction mode. The interactive intelligent sports system 109 receives sensor data from a plurality of sensors 105 attached to the player or embedded in a golf club.

In step 303, the interactive intelligent sports system 109 processes the sensor data in real-time to determine the playing technique information. In one example embodiment, the sensor data comprises information pertaining to the playing technique of the golf player as gathered by the sensors 105a-105n. The interactive intelligent sports system 109 then performs an analysis of sensor data with respect to course and conditions.

In step 305, the interactive intelligent sports system 109 retrieves baseline information for the player. In one embodiment, the baseline information includes historical playing technique information of the player as well as other information (e.g., heath or medical information) that may impact the player's technique or performance. In one example embodiment, the interactive intelligent sports system 109 processes the golf swing pattern of the player over a period of time to generate the baseline information that can be used toward determining a recommended golf swing (i.e., target playing technique) and associated instructions for corrective measures towards that ideal or target golf swing. Such baseline information and related analysis assist in revealing any nuances or patterns associated with the playing technique for an individual player and/or group of players. In another embodiment, the baseline information includes target playing technique information associated with another player, such as a golf professional. In one embodiment, the target playing technique information can represent the "best" technique that the user has demonstrated over a series of swings and/or time.

In step 307, the interactive intelligent sports system 109 compares the playing technique information with the baseline information. In one example embodiment, the interactive intelligent sports system 109 compares, in real-time, the player's swing to a pre-recorded or simulated swing, which can serve as a baseline. Such a baseline can be based on various criteria (e.g., latest swing, best swing, good swing in similar environmental conditions, etc.). In one example embodiment, the interactive intelligent sports system 109 determines whether the playing technique of the golf player satisfies a predetermined threshold level based on the comparison. In one embodiment, a playing technique does not satisfy a predetermined threshold level if the player bends his/her wrist beyond a prescribed limit. In another example embodiment, the playing technique does not satisfy a predetermined threshold level if the player swings the golf club beyond a recommended range. In a further example embodiment, playing technique does not satisfy a predetermined threshold level if the user exerts excessive gripping pressure, i.e., an improper golf grip, during a swing.

In step 309, the interactive intelligent sports system 109 generates, in real-time with the engagement of the sports activity (e.g., golf play), an instructional message to modify playing technique of the player based on the comparison. Thereafter, in step 311, the interactive intelligent sports system 109 initiates presentation, during the sports activity, of the instructional message to a user interface of a device accessible by the player. Such instruction message can be conveyed in any number of ways; the instruction, is transmitted, e.g., via UE 101 or any device that can provide aural or video information to the player. For instance, such a device may be on the player or nearby, as in a golf cart. The player watches and listens to the coaching instructions and attempts to carry out the instructions; the execution of these instructions can be monitored by the system 109 for further instructions.

Figure 3B:
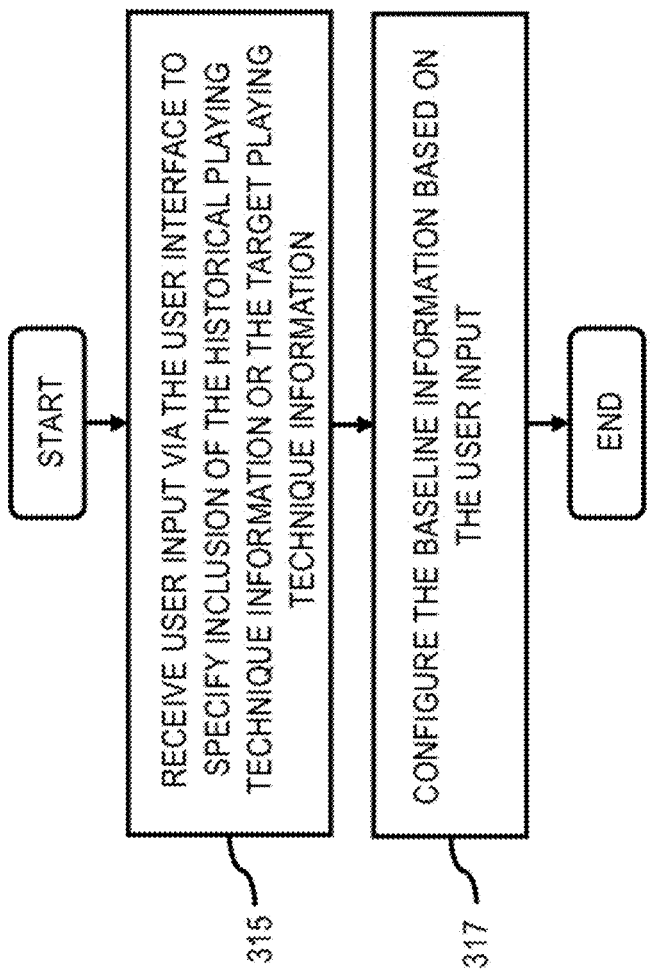
FIG. 3B is a flowchart of a process for configuring baseline information, according to one embodiment.

FIG. 3B is a flowchart of a process for configuring baseline information, according to one embodiment. In one embodiment, the interactive intelligent sports system 109 performs the process 313 and is implemented in, for instance, a chip set including a processor and a memory as shown in FIG. 11.

In step 315, the interactive intelligent sports system 109 receives user input via the user interface to specify inclusion of the historical playing technique information or the target playing technique information. In one example embodiment, historical playing technique information comprises playing style information, playing pattern information, playing progress information, or a combination thereof of the player. In one example embodiment, target playing technique information is associated with an expert player, and the playing technique information of the player is modeled according to the target playing technique information of the expert player.

In step 317, the interactive intelligent sports system 109 configures the baseline information based on the user input. In one example embodiment, the interactive intelligent sports system 109 processes the golf swing pattern of a player over a period of time to generate baseline information about the player that can be used toward determining a recommended golf swing. In another embodiment, the baseline information includes target playing technique information associated with another player.

Figure 3C:
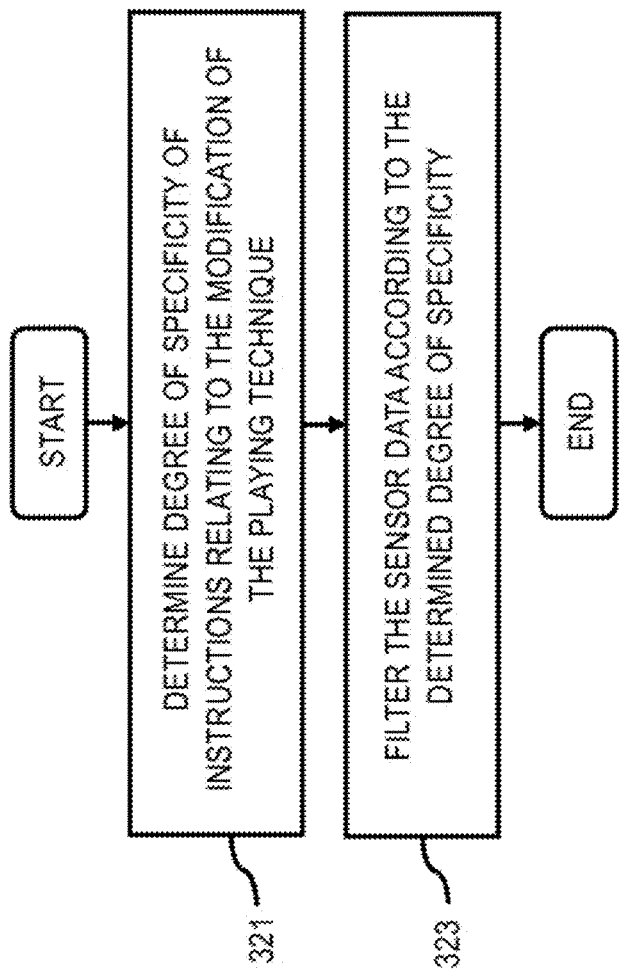
FIG. 3C is a flowchart of a process for filtering sensor data based on the specificity of instructions, according to one embodiment.

FIG. 3C is a flowchart of a process for filtering sensor data based on the specificity of instructions, according to one embodiment. In one embodiment, the interactive intelligent sports system 109 performs the process 319 and is implemented in, for instance, a chip set including a processor and a memory as shown in FIG. 11.

In step 321, the interactive intelligent sports system 109 determines the degree of specificity of instructions relating to the modification of the playing technique. In one example embodiment, the interactive intelligent sports system 109 may process the playing technique of the player to determine the required degree of instructions. In one example embodiment, the interactive intelligent sports system 109 determines that the player bends his/her wrist beyond a prescribed limit, swings the golf club beyond a recommended range, and exerts excessive gripping pressure, i.e., an improper golf grip, during a swing. Subsequently, the interactive intelligent sports system 109 determines that the player requires detailed feedback.

In step 323, the interactive intelligent sports system 109 filters the sensor data according to the determined degree of specificity. In one embodiment, the generation of the instructional message is based on the filtered sensor data. In one example embodiment, the interactive intelligent sports system 109 determines that the player is a beginner and requires detailed feedback. The system 109 processes maximum sensor data to generate detailed feedback to improve the playing technique of the player. In one embodiment, the interactive intelligent sports system 109 determines the progress of the player based on the periodic reports pertaining to the performance of the player. The degree of instructions required to improve the playing technique of the player is based on the progress of the player.

Figure 3D:
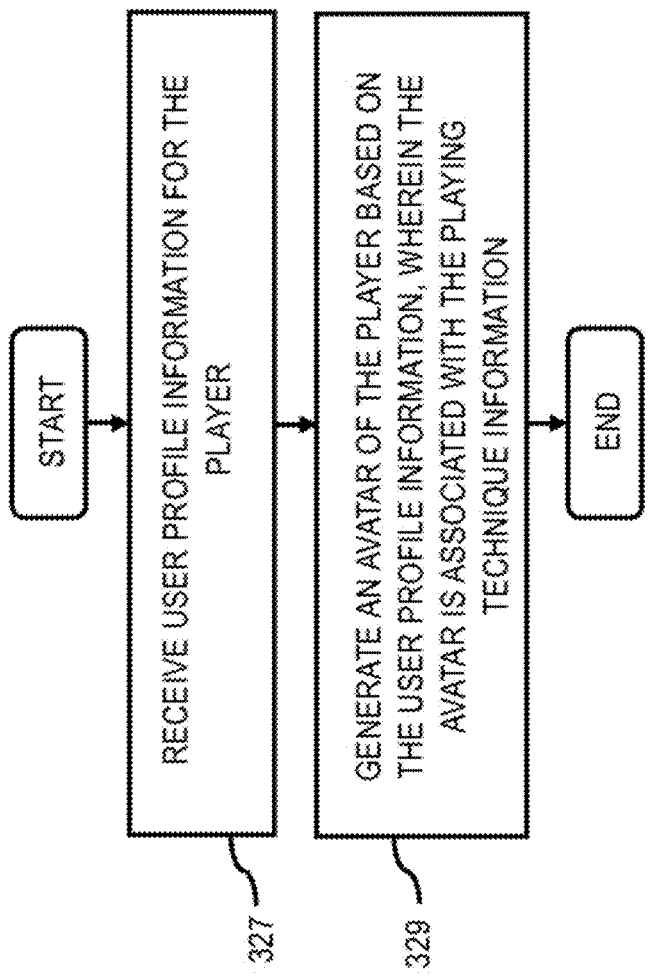
FIG. 3D is a flowchart of a process for generating a graphical representation of the player, according to one embodiment.

FIG. 3D is a flowchart of a process for generating a graphical representation of the player, according to one embodiment. In one embodiment, the interactive intelligent sports system 109 performs the process 325 and is implemented in, for instance, a chip set including a processor and a memory as shown in FIG. 11.

In step 327, the interactive intelligent sports system 109 receives user profile information for the player. In one example embodiment, a player is presented with a set of questionnaires while registering with the service, and system 109 may use the questionnaires to generate a profile for the player. In another example embodiment, the player may choose their profile based on their experience level. In a further example embodiment, the interactive intelligent sports system 109 may automatically designate a profile to the player based on their performance.

In step 329, the interactive intelligent sports system 109 generates an avatar of the player based on the user profile information. In one embodiment, the avatar is associated with the playing technique information of the player. In one example embodiment, characteristics of the user, e.g., likeness or true image, swing and playing style, are exported to play virtual courses as in a video game or simulator.

Figure 3E:
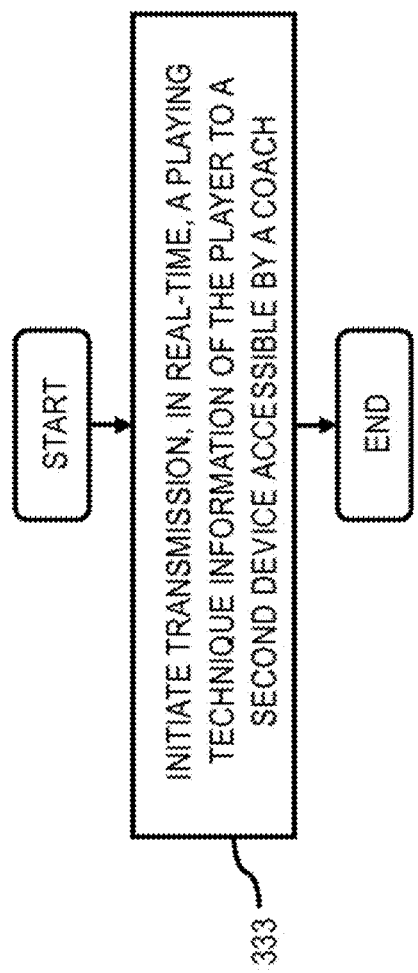
FIG. 3E is a flowchart of a process for generating real-time feedback from a coach, according to one embodiment.

FIG. 3E is a flowchart of a process for generating real-time feedback from a coach, according to one embodiment. In one embodiment, the interactive intelligent sports system 109 performs the process 331 and is implemented in, for instance, a chip set including a processor and a memory as shown in FIG. 11.

In step 333, the interactive intelligent sports system 109 initiates transmission, in real-time, the playing technique information of the player to a second device accessible by a coach. In one example embodiment, the interactive intelligent sports system 109 may present live movements of the player during golf play in a user interface of a UE 101 associated with the coach. In another example embodiment, the interactive intelligent sports system 109 may superimpose detailed statistics of the player over the display, i.e., live movements of the player. Thereafter, the interactive intelligent sports system 109 provides, in real-time with the engagement of the sports activity, instructional message, e.g., coaching instructions, to modify the playing technique of the player in the UE 101 associated with the player. In one embodiment, the instructional message is provided as auditory feedback to the player.

Figure 3F:
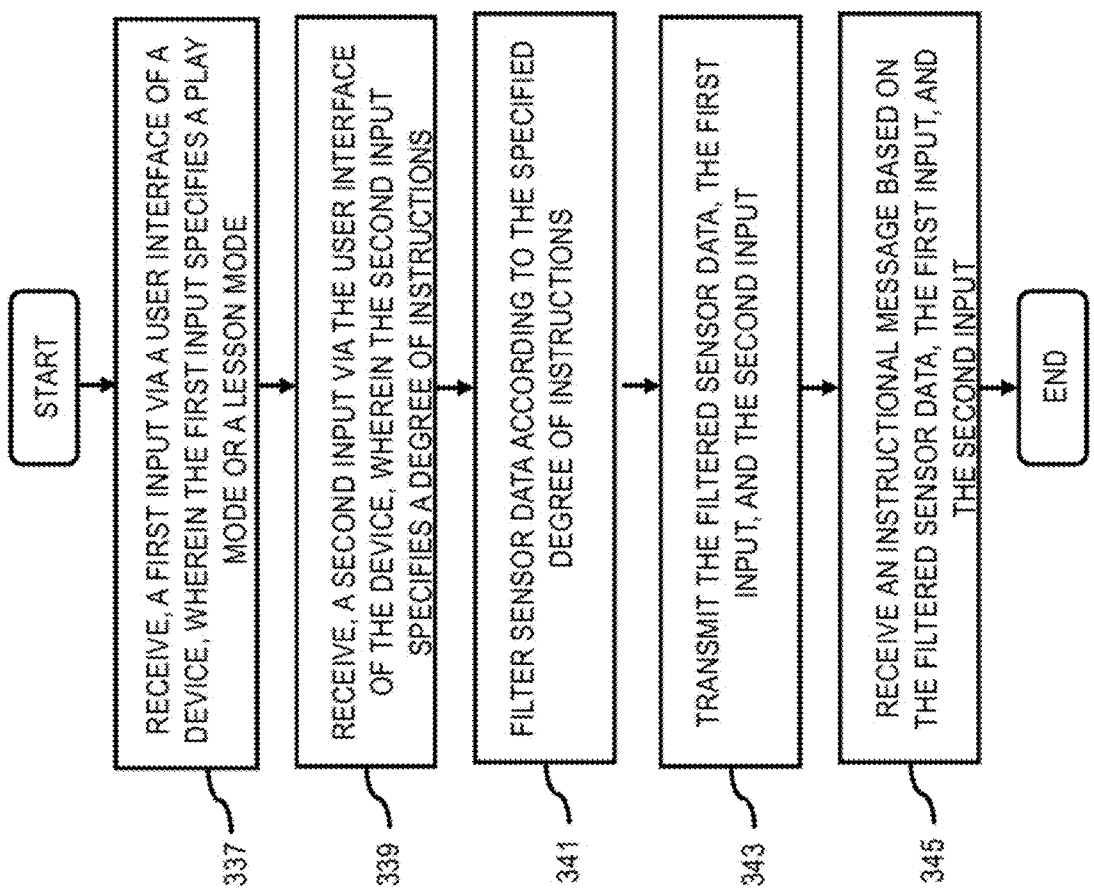
FIG. 3F is a flowchart of a process for generating an instructional message based on user input, according to one embodiment.

FIG. 3F is a flowchart of a process for generating an instructional message based on user input, according to one embodiment. In one embodiment, the interactive intelligent sports system 109 performs the process 335 and is implemented in, for instance, a chip set including a processor and a memory as shown in FIG. 11.

In step 337, interactive intelligent sports system 109 receives, a first input via a user interface of a device, wherein the first input specifies a play mode or a lesson mode. In one example embodiment, a player may select a play mode via his/her UE 101, whereupon the interactive intelligent sports system 109 can virtualize the actual play on the golf course; in this manner, the user can play against current online players, or past/recorded plays of other players (including the user's own past game). The system 109 may then provide instructional messages to the subject player to outperform the other players. Furthermore, system 109 may provide performance statistics of the player and the other players in the user interfaces of the UE 101. In another embodiment, a player may select a lesson mode via his/her UE 101, whereupon system 109 may prioritize the "real-time" nature of the processing of sensor data. The system 109 may then provide instructional messages to enhance the playing technique of the player.

In step 339, the interactive intelligent sports system 109 receives, a second input via the user interface of the device, wherein the second input specifies a degree of instructions. In one embodiment, the specified degree of instructions relates to a modification of a playing technique of the user during a sports activity, e.g., a golf play. In one example embodiment, a novice player may request for detailed feedback, whereas an expert player may request basic feedback.

In step 341, the interactive intelligent sports system 109 filters sensor data according to the specified degree of instructions. In one example embodiment, a professional player requesting for basic feedback, e.g., less detailed feedback, requires fewer sensor data and shorter processing time. Subsequently, system 109 can be selective in processing only certain sensor data that is required to produce the feedback. In another example embodiment, a novice player requesting detailed feedback mandates system 109 to process more sensor data and higher processing time.

In step 343, filtered sensor data, the first input, and the second input is transmitted to the interactive intelligent sports system 109 for further processing. Thereafter, in step 345, the interactive intelligent sports system 109 provides an instructional message based on the filtered sensor data, the first input, and the second input. In one example embodiment, a player selects "lesson mode" via UE 101a, and requests for basic feedback on his/her playing technique. The system 109 may selectively process certain sensor data required to generate a basic instructional message for the player. The player receives, in real-time, the basic instructional message via UE 101a.

Figure 3G:
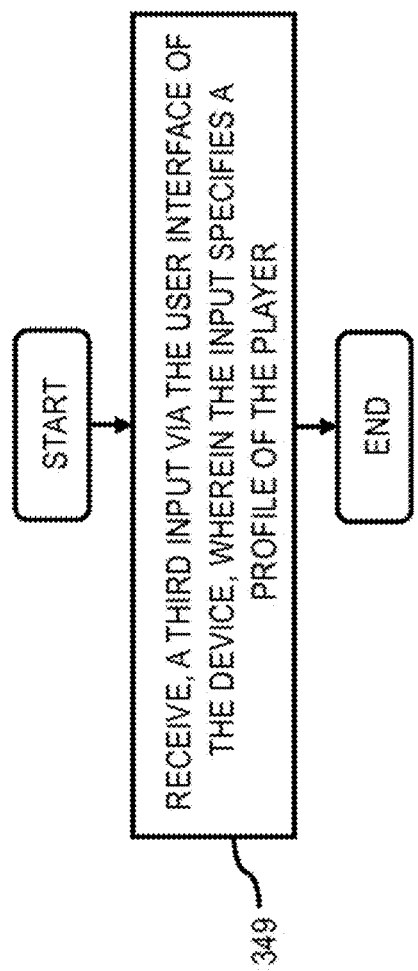
FIG. 3G is a flowchart of a process for determining a degree of specificity of instructions based on a user profile, according to one embodiment.

FIG. 3G is a flowchart of a process for determining a degree of specificity of instructions based on a user profile, according to one embodiment. In one embodiment, the interactive intelligent sports system 109 performs the process 347 and is implemented in, for instance, a chip set including a processor and a memory as shown in FIG. 11.

In step 349, the interactive intelligent sports system 109 receives, a third input via the user interface of the device, wherein the input specifies a profile of the player. In one embodiment, the profile comprises a novice player, an intermediate player, or an expert player. In one example embodiment, players may launch a golf application 103 resident in their respective UE 101 to select a profile based on their level of experience. A beginner may specify his/her profile as a novice player whereas an experienced player may specify his/her profile as a professional player. Thereafter, the interactive intelligent sports system 109 determines a degree of specificity of instructions relating to the modification of the playing technique based on the profile of the player. In one example embodiment, a novice player may be provided with a detailed instructional message compared to a professional player.

Figure 3H:
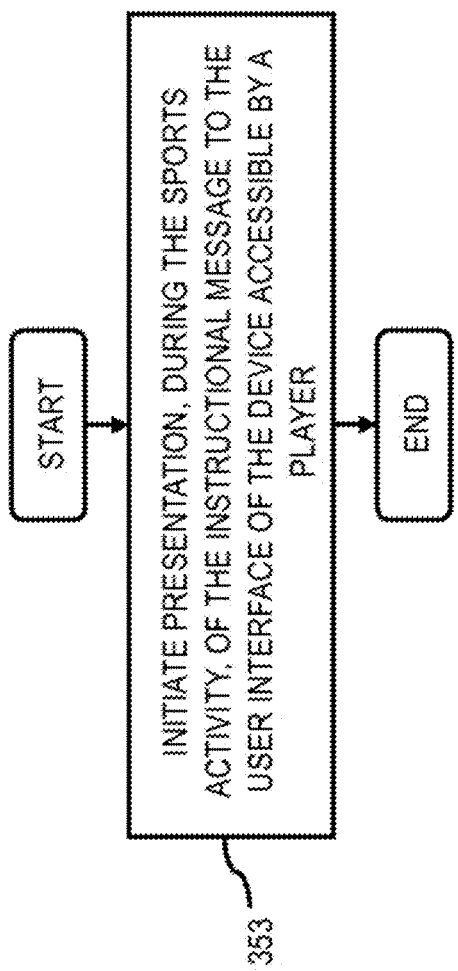
FIG. 3H is a flowchart of a process for presenting an instructional message in a user interface of a device accessible by a player, according to one embodiment.

FIG. 3H is a flowchart of a process for presenting an instructional message in a user interface of a device accessible by a player, according to one embodiment. In one embodiment, the interactive intelligent sports system 109 performs the process 351 and is implemented in, for instance, a chip set including a processor and a memory as shown in FIG. 11.

In step 353, the interactive intelligent sports system 109 initiates presentation, during the sports activity, of the instructional message to the user interface of the device accessible by a player. In one example embodiment, the interactive intelligent sports system 109 provides an aural rendition of the instructional message in a UE 101 of the player during golf play. In another example embodiment, the interactive intelligent sports system 109 presents an aural and a visual rendition of the instructional message in a UE 101 of the player during a golf play.

Figure 4:
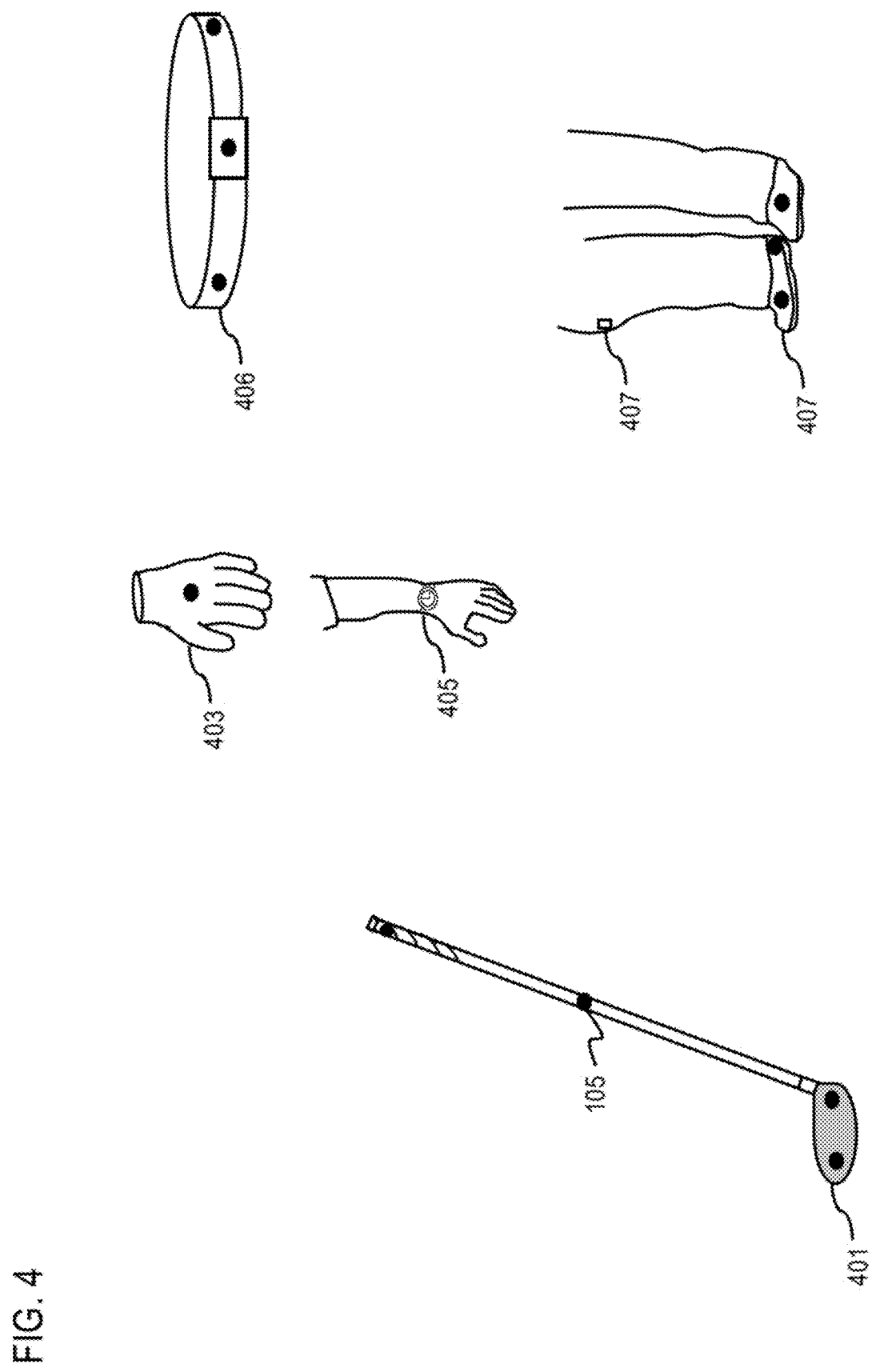
FIG. 4 is a diagram that shows one or more sensors affixed to the player and/or equipment, according to various example embodiments.

FIG. 4 is a diagram that shows one or more sensors affixed to the player and/or equipment, according to various example embodiments. In this example, a golf club 401 of a player can be deployed with one or more sensors 105 along the shaft and/or club head to detect golf swing of a player, hand position of a player, body posture of a player, etc. It is contemplated that the sensor(s) 105 can be affixed to the club 401 directly or through a physical mechanism (not shown) that allows the sensor 105 to be readily positioned and repositioned along the club 401. In one embodiment, sensor 105 is an acceleration sensor to measure the acceleration of the shaft. In another embodiment, the golf club 401 comprises electromagnetic sensors and/or ultrasound sensors as well as pressure sensors to measure grip pressure applied by the players and/or hand position of a user.

In one embodiment, the user may have a sensor embedded within a golf glove 403 to detect hand positioning and grip during a swing. In this way, the interactive intelligent sports system 109 may analyze hand positioning data and grip data to determine where a user's hand is relative to the orientation of a user's body.

In another embodiment, a wrist sensor 405, e.g., a smartwatch that has a sensor, a separate sensor affixed to a wristwatch, exercise wristband, etc., can output data to help detect hand movements, e.g., wrist movement, arm positioning, etc., during a golf swing. In another embodiment, wrist sensor 405 via sensors 105 on the club 401 triggers a signal to the interactive intelligent sports system 109 when a golfer bends his/her wrists improperly, e.g., bending wrist beyond a selected limit, during a swing. In one embodiment, sensors 105 may be affixed to footwear/apparel (e.g., headgear, cap, shirt and/or pants) 407 and/or a belt/waistband 406 (which may employ one or more sensors distributed along the front side of the belt/waistband as well as the backside) to collect posture data. In one embodiment, sensors 105 affixed to footwear/apparel may be applicable to other sports, e.g., sensors 105 may detect body movement and technique forms during other sports activities, e.g., martial arts training. It is noted that the various deployment of sensors can be determined based on the preference of the player with respect to the detail level of the instructions desired. For instance, if the player is not concerned about body position or posture, but clubhead speed and angle of the clubface, then only sensors on the club 401 may be needed.

Figure 5:
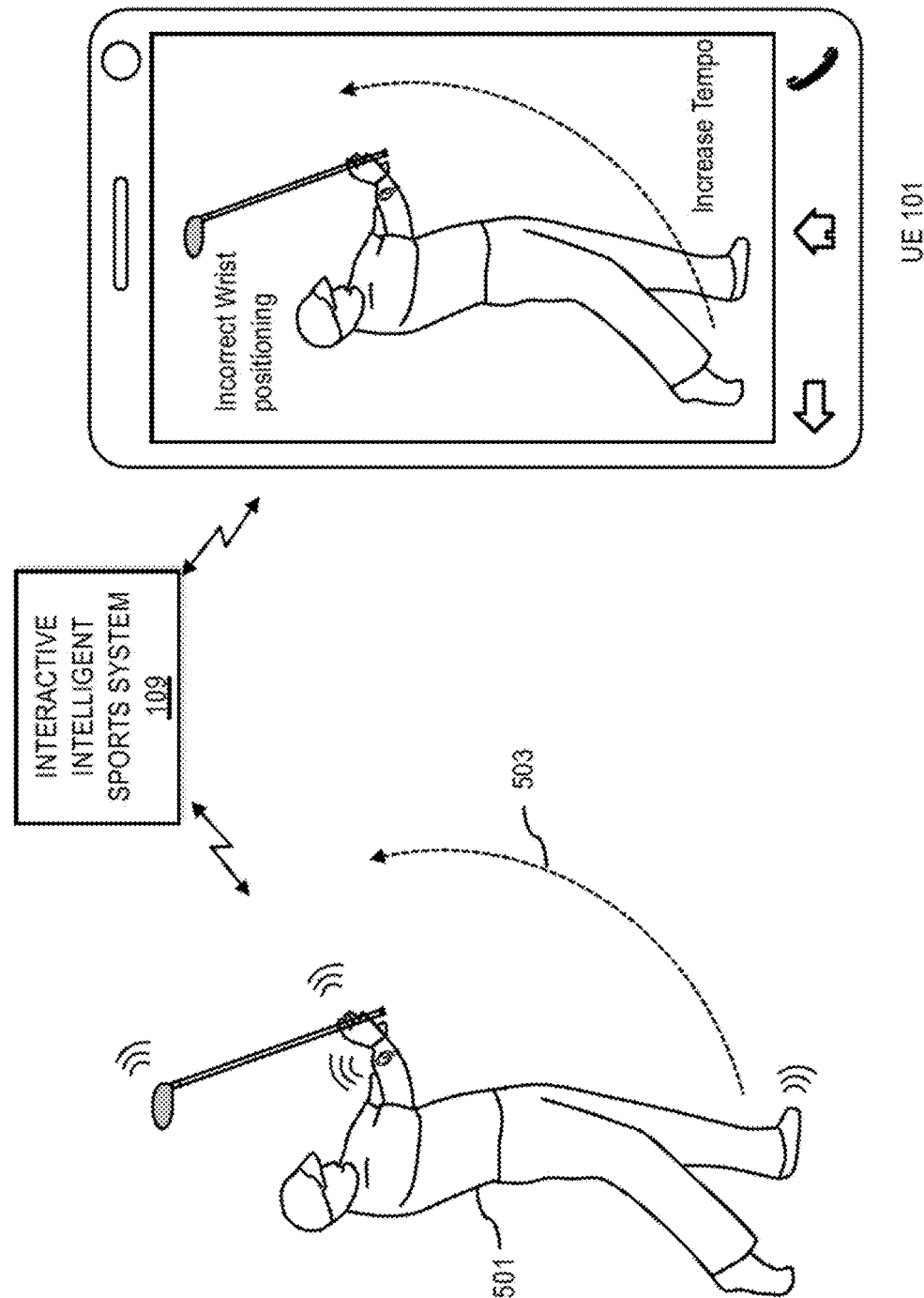
FIG. 5 is a diagram that shows a scenario wherein real-time feedback relates to swing analysis during golf play, according to various example embodiments.

FIG. 5 is a diagram that shows a scenario wherein real-time feedback relates to swing analysis during golf play, according to various example embodiments. In this embodiment, player 501 is playing golf, and selects to the real-time instruction mode via UE 101. In the real-time instruction mode, the interactive intelligent sports system 109 receives sensor data from the arrangement of sensors shown in FIG. 4. The interactive intelligent sports system 109 performs an analysis of the sensor data to determine whether the golf swing 503 of player 501 is proper with respect to course and conditions. It is noted that the UE 101 itself can complement the host of sensors with its own information, e.g., images; if the camera of the UE 101 is to be utilized, the UE 101 may be mounted onto the player's golf bag or golf cart. In one embodiment, while performing a full swing 503, if the wrists hinge in any other direction other than parallel to the forearm during the backswing, the player is said to have either opened or closed the clubface causing the ball to hook or slice. The interactive intelligent sports system 109 determines that the wrists of player 501 are not parallel to the forearm, whereupon an appropriate coaching instruction is formulated, e.g., aural or visual instructions to improve the wrist motion of player 501 is transmitted to the UE 101. In another example embodiment, in swing intensive sporting activities, such as golf, it is difficult to perfect a swing and repeat it consistently. In golf, for example, proper golf swing tempo ensures that golf club head velocity and golf club head position are optimized during a golf swing. As such, the system 109 can help the golfer to improve consistency with respect to proper swing tempo. The real-time feedback may be to instruct the player to increase or decrease swing tempo. In this example, the interactive intelligent sports system 109 determines that the swing tempo of player 501 should be increased, whereby an aural or visual instruction to increase the swing tempo is transmitted to the UE 101 for presentation to the player. In one embodiment, aural or visual instructions may be presented in a live video by a virtual reality device, e.g., UE 101. Also, the UE 101 may employ other indicators to indicate the tempo instruction, e.g., flashing an LED light at a fast rate. In another embodiment, the interactive intelligent sports system 109 may transmit performance data derived from the sensor data to a coach based on a determination that the player does not show any improvement over a specified time period. Thereafter, the coach can develop drills to improve the player's performance; the execution of these drills may then be monitored and tracked by the system 109.

Figure 6:
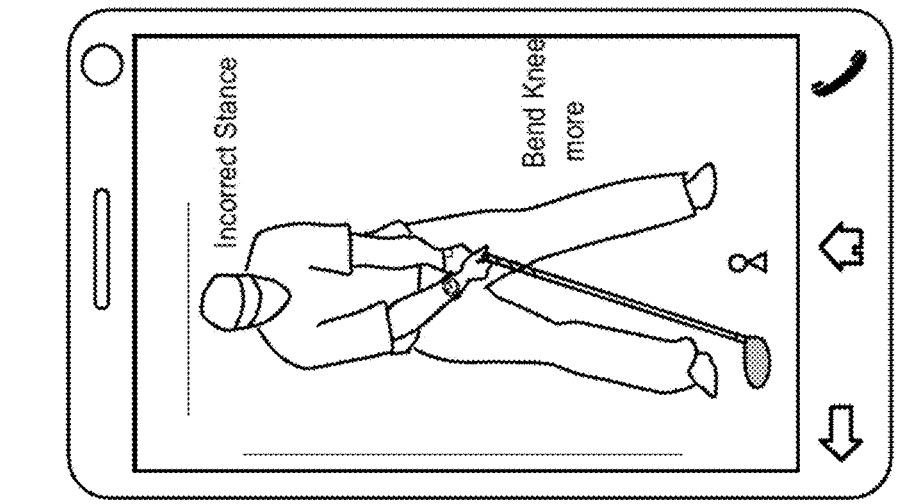
FIG. 6 is a diagram that shows a scenario wherein real-time posture analysis is performed during golf play, according to various example embodiments.
Figure 6:
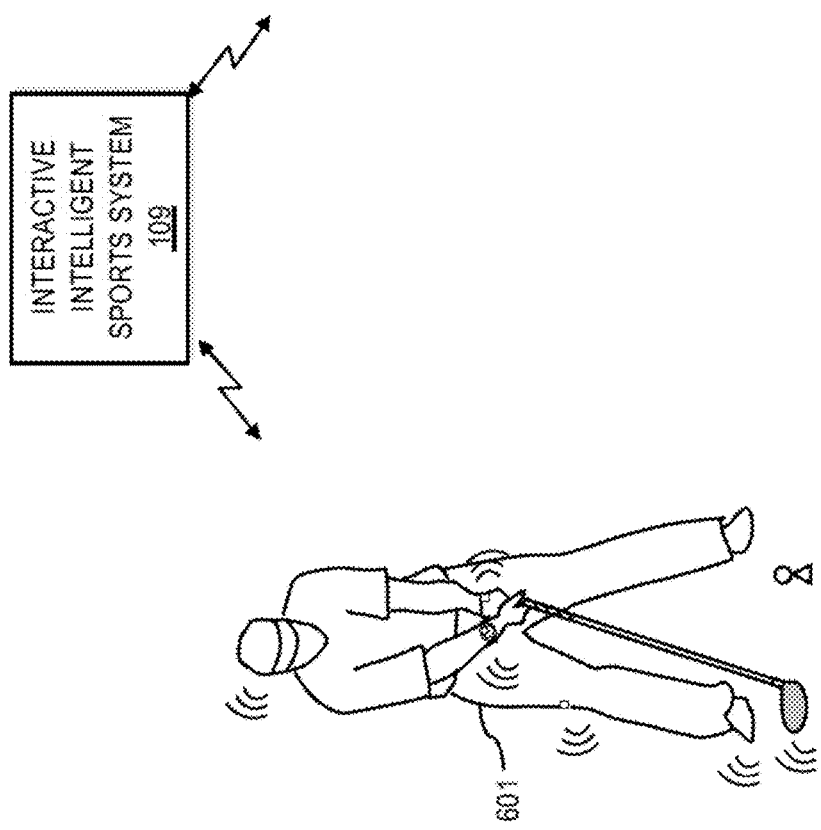

FIG. 6 is a diagram that shows a scenario wherein real-time posture analysis is performed during golf play, according to various example embodiments. In this example, the system 109 provides instructions to correct the player's stance and position. As such, the interactive intelligent sports system 109 analyzes sensor data to determine whether the stance, e.g., body position, of player 501 is proper with respect to the course characteristics (e.g., topology). A golfer's stance factors significantly to the leg, hand, and arm movements during the swing, and thus is a key element in attaining a controlled hit. In one embodiment, the correctness of a swing is indicative of proper body position and proper body motion, e.g., golfer's legs are generally apart, slightly bent knees, and seeks to swing the club with his arms through a wide arc to contact the ball and one's knees are bent. In this example, the interactive intelligent sports system 109 determines that the player has improper body position, e.g., unbent knees, of player 601 resulting in an improper swing motion. Thereafter, the interactive intelligent sports system 109 provides real-time body motion information to player 601, e.g., slightly bend knees.

Figure 7:
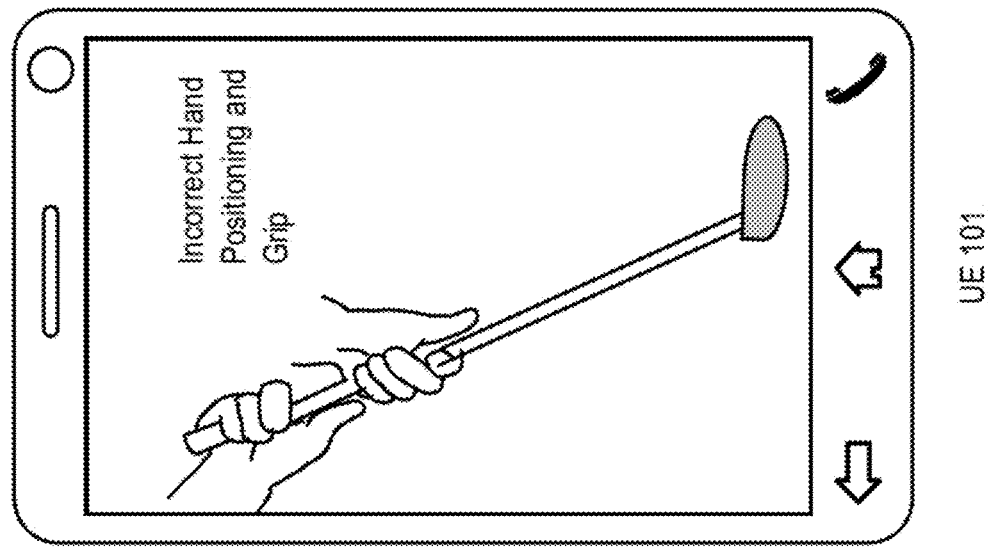
FIG. 7 is a diagram that shows a scenario wherein real-time hand position and grip analysis is performed during golf play, according to various example embodiments.
Figure 7:
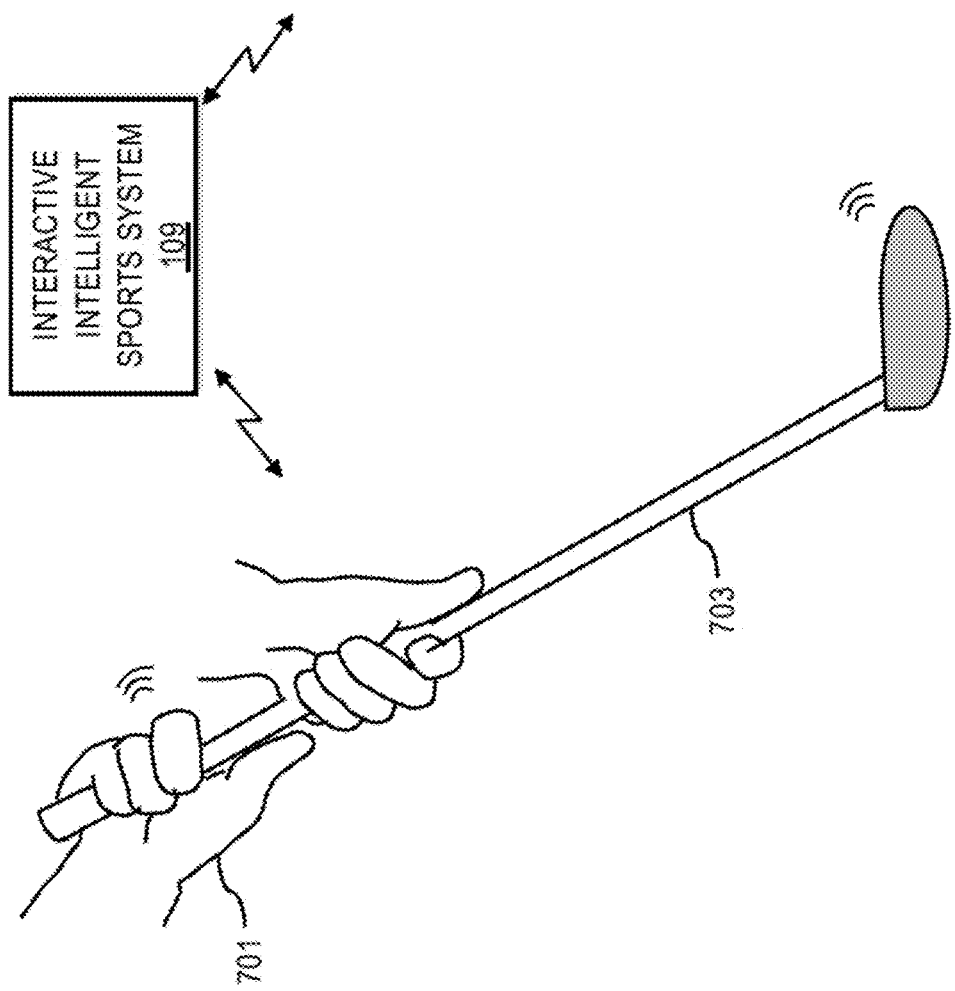

FIG. 7 is a diagram that shows a scenario wherein real-time hand position and grip analysis is performed during golf play, according to various example embodiments, according to various example embodiments. Hand placement and/or handgrip on a golf club is an important factor in attaining a good golf swing and for influencing the distance and direction of a golf ball. Here, the interactive intelligent sports system 109 performs an analysis of sensor data (including for example image information from the UE 101) to determine whether the hand position and grip of player 701 on the golf club 703 is proper. The interactive intelligent sports system 109 determines that the player has an incorrect hand position and grip on the golf club 703 resulting in an improper swing motion. Thereafter, the interactive intelligent sports system 109 provides real-time feedback to player 701, e.g., loosen your grip, top hand should slightly overlap the first hand, etc.

Figure 8:
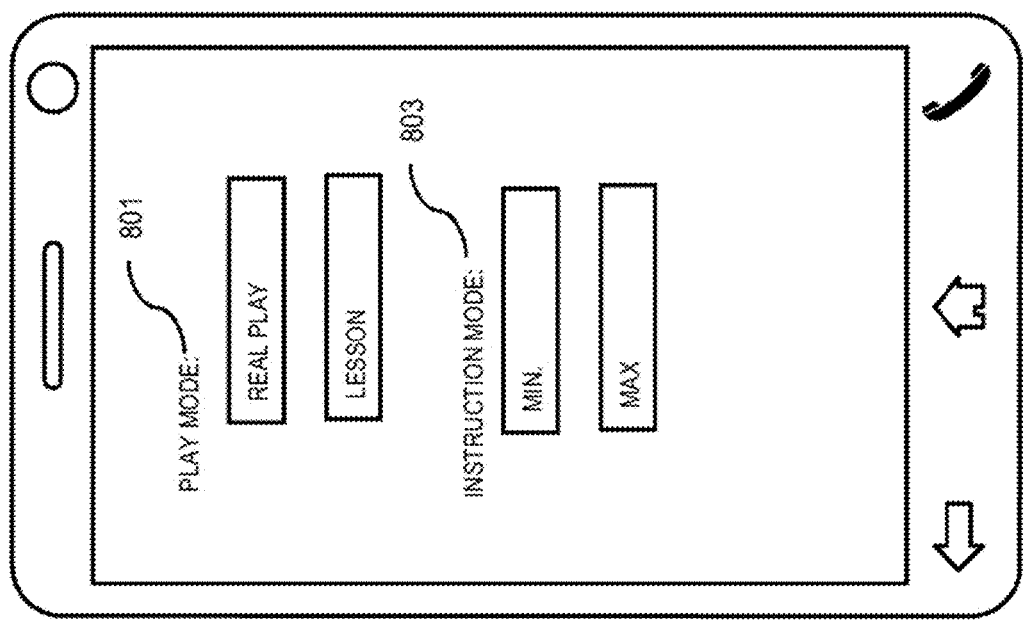
FIG. 8 is a diagram of a user interface providing different modes for feedback, according to various example embodiments.

FIG. 8 is a diagram of a user interface providing different modes for feedback, according to various example embodiments. In one embodiment, the interactive intelligent sports system 109 employs various application programming interfaces (APIs) or other function calls corresponding to the application 103 of UE 101; thus enabling the display of graphics primitives such as menus, data entry fields, etc., for generating the user interface elements. Still further, various user interface elements may be configured to operate in connection with augmented reality (AR) processing techniques, wherein various different applications, graphic elements, and features may interact. In one embodiment, UE 101 presents a graphical user interface (GUI) that includes a section 801 to specify the mode of play: real play or lesson. This selection will allow the system 109 to determine how to prioritize the "real-time" nature of the processing of sensor data. In "lesson" mode, the player may not be in such a hurry to move along play, and thus, the system 109 can factor this in its analysis. Also, the GUI may provide a section (not shown), to select play in a virtual environment. Moreover, the GUI provides an area 803 to specify the level of detail for the instructions. If the player is very skilled, the system 109 need only provide a few tips, while a novice player may need greater instructions about many aspects of the swing. Consequently, the user can toggle on a minimal level or a maximum level. Although two levels are shown, it is contemplated that more levels can be selectable: novice, intermediate, and advance.

Figure 9A:
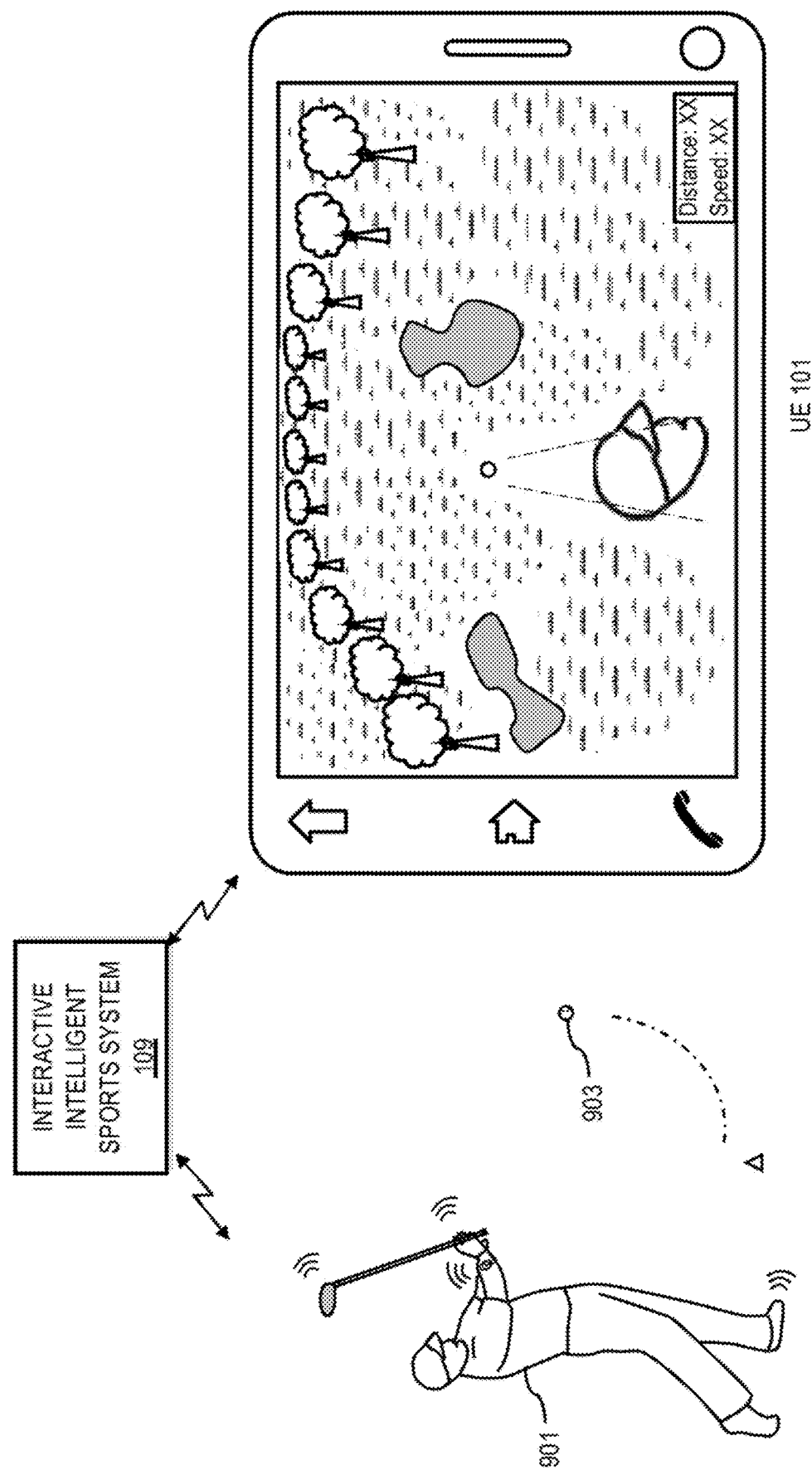
FIG. 9A is a diagram that shows a virtual golf simulation environment on a mobile device, according to various example embodiments.

FIG. 9A is a diagram that shows a virtual golf simulation environment on a mobile device, according to various example embodiments. The user may wish to have the user's real play on the course be "virtualized" into a video game with the player's avatar. The interactive intelligent sports system 109 then allows a user to navigate through the virtual reality world while receiving feedback during play. In this manner, the user can play against players who are currently online, or past/recorded plays of other players (including the user's past game). In one embodiment, one or more sensors 105 are housed within a golf ball 903. These sensors are configured to calculate directions, e.g., angle of ascent or descent, acceleration, e.g., spin rate, time and distance of roll, ball velocity, etc., and the distance traveled, e.g., distance to the pin, by the golf ball 903. Furthermore, these sensors are configured to determine the location of golf ball 903 in real-time, thereby providing golfers with an effective medium for locating a lost golf ball. In one example embodiment, the same applies to other sports, e.g., basketball, football, table tennis, squash, etc., where sensors 105 are embedded within the balls of respective sports and may monitor locality information, e.g., whether the ball was within or outside of the playing area.

Figure 9B:
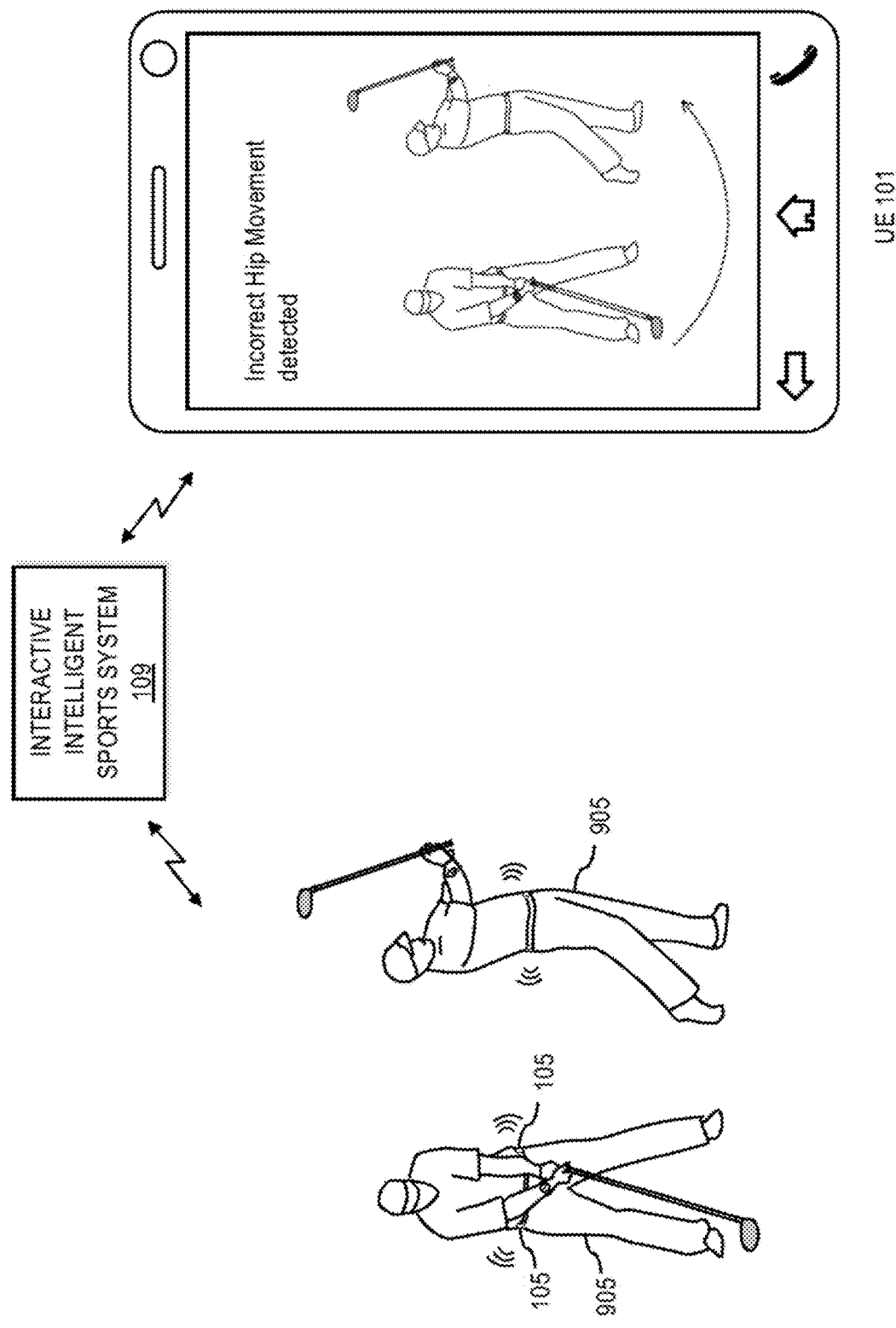
FIG. 9B is a diagram that shows a scenario wherein real-time analysis is performed on hip-movements of players during golf play, according to various example embodiments.

FIG. 9B is a diagram that shows a scenario wherein real-time analysis is performed on hip-movements of players during golf play, according to various example embodiments. During golf play, the torsional force provided by the torso twist and the efficient transmission of that energy to the ball is of utmost importance, and a common mistake during a golf swing is excessive hip movement, both in rotation and lateral sway. In one embodiment, sensors 105 embedded in a belt, waistband, or mounted on the hip of player 905 measures hip rotation of player 905 during a golf swing. Thereafter, the interactive intelligent sports system 109 determines whether the hip movement of player 905 is correct based on the processing of sensor information provided by sensors 105. In this example, the interactive intelligent sports system 109 determines that player 905 has excessive hip movement. Thereafter, the interactive intelligent sports system 109 provides in real-time a correct hip motion information to player 905, e.g., slower hip sway. In another example embodiment, the interactive intelligent sports system 109 determines player 905 has less rotation of the hips during a golf swing compared to an average user, whereupon the interactive intelligent sports system 109 may recommend exercises to improve the flexibility of the hips.

Figure 9C:
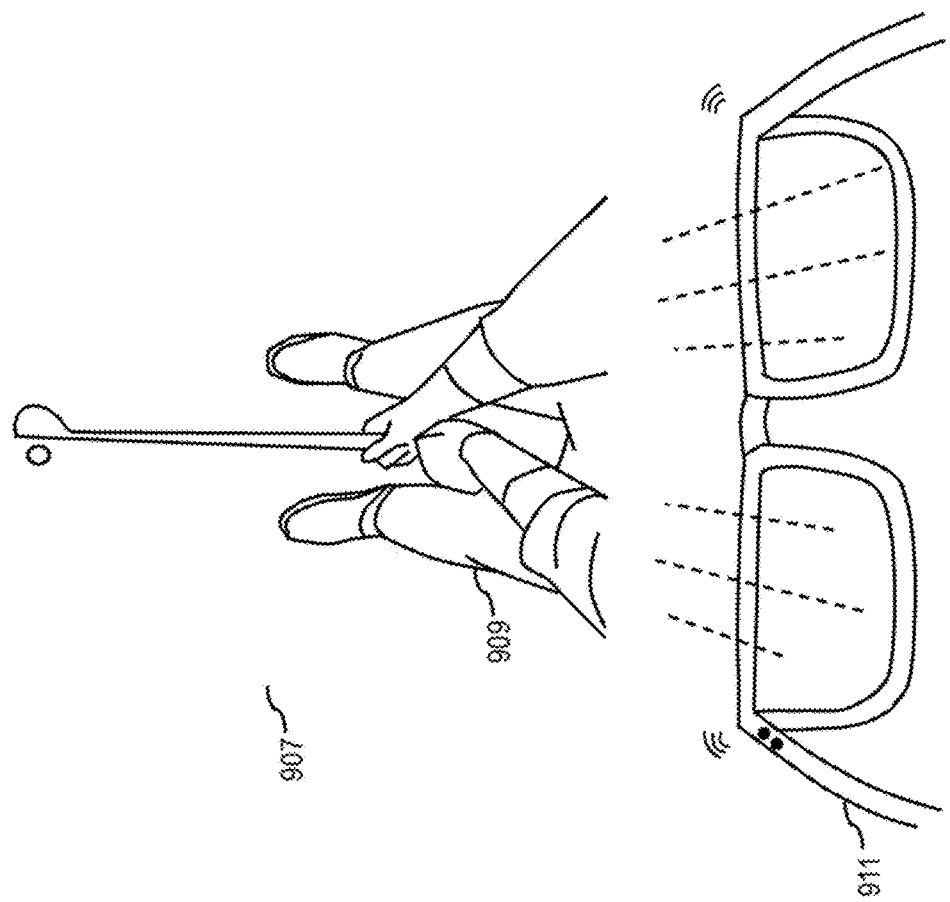
FIG. 9C is a diagram that shows a field-of-view captured by an augmented reality display device during golf play, according to various example embodiments.

FIG. 9C is a diagram that shows a field-of-view captured by an augmented reality display device during golf play, according to various example embodiments. In one example embodiment, field-of-view 907 from the viewpoint of player 909 is recorded in real-time by augmented reality display devices 911, e.g., smart glasses, and transmitted to the interactive intelligent sports system 109. The interactive intelligent sports system 109 may display the recording in smart glasses of other players in real-time based on request. The smart glass 911 comprises one or more sensors 105, e.g., audio sensors, to receive aural instructions from the players. That is, the smart glass 911 can provide interactive voice response commands from the wearer to switch to various views—the scores, ball flight, other users' field-of-views, etc. In another embodiment, the smart glass 911 can switch to augmented reality views based on voice commands. In one example embodiment, the smart glass 911 may be equipped with a microphone to pick-up voice commands from a user, e.g., "switch to augmented reality mode." The voice command is then transmitted, in real-time, to the interactive intelligent sports system 109 for processing, and executing an action in response to the voice command, e.g., switch to the augmented reality mode from the current view. In one example embodiment, the interactive intelligent sports system 109 captures a field-of-view of the player via an augmented reality display device 911 during a golf play. Then, the interactive intelligent sports system 109 transmits, in real-time, the captured field-of-view of the player to the augmented reality display device of another player.

Figure 9D:
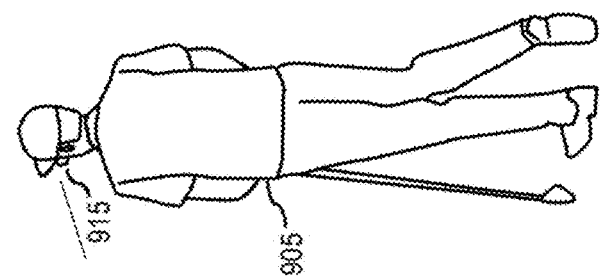
FIG. 9D is a diagram that shows a perspective view for one or more users wearing augmented reality display devices, according to various example embodiments.
Figure 9D:
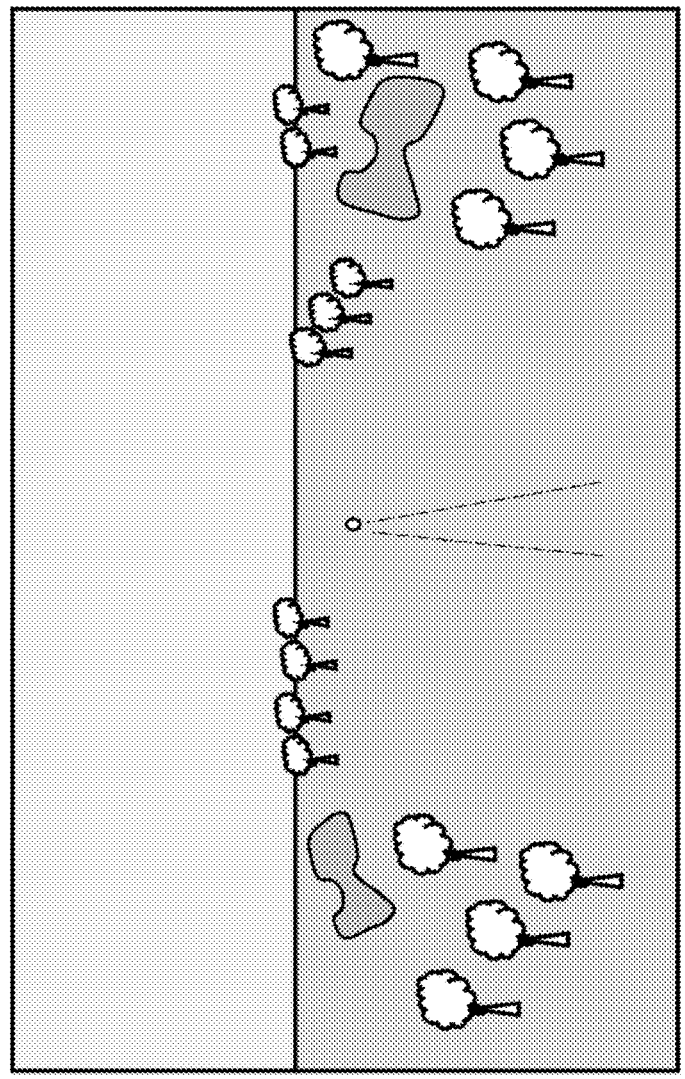
Figure 9D:
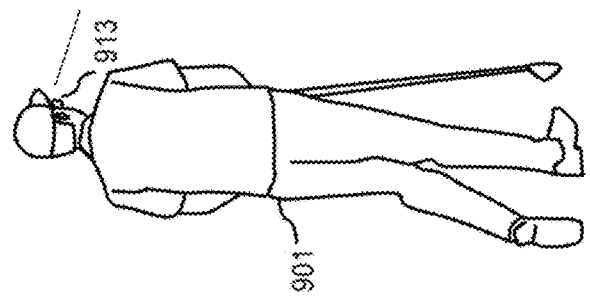

FIG. 9D is a diagram that shows a perspective view for one or more users wearing augmented reality display devices, according to various example embodiments. In this manner, the system 109 can provide the user with views of golf ball flight during augmented reality play. This capability is particularly useful when the user has an obstructed view of the ball flight. In addition, the system 109 can support switching to another player's point-of-view (POV). In one example embodiment, the interactive intelligent sports system 109 determines a point-of-view (POV) of the player is obstructed during a golf play. Thereafter, the interactive intelligent sports system 109 switches, in real-time, the obstructed POV of the player with an unobstructed POV of another player in the augmented reality display device of the player. In the example of FIG. 9C, players 901 and 905 can observe the putting by player 909 via their respective augmented reality display devices 913 and 915.

The processes described herein for providing real-time feedback during a sports activity (e.g., golf play) based, at least in part, on analysis of sensor information may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 10:
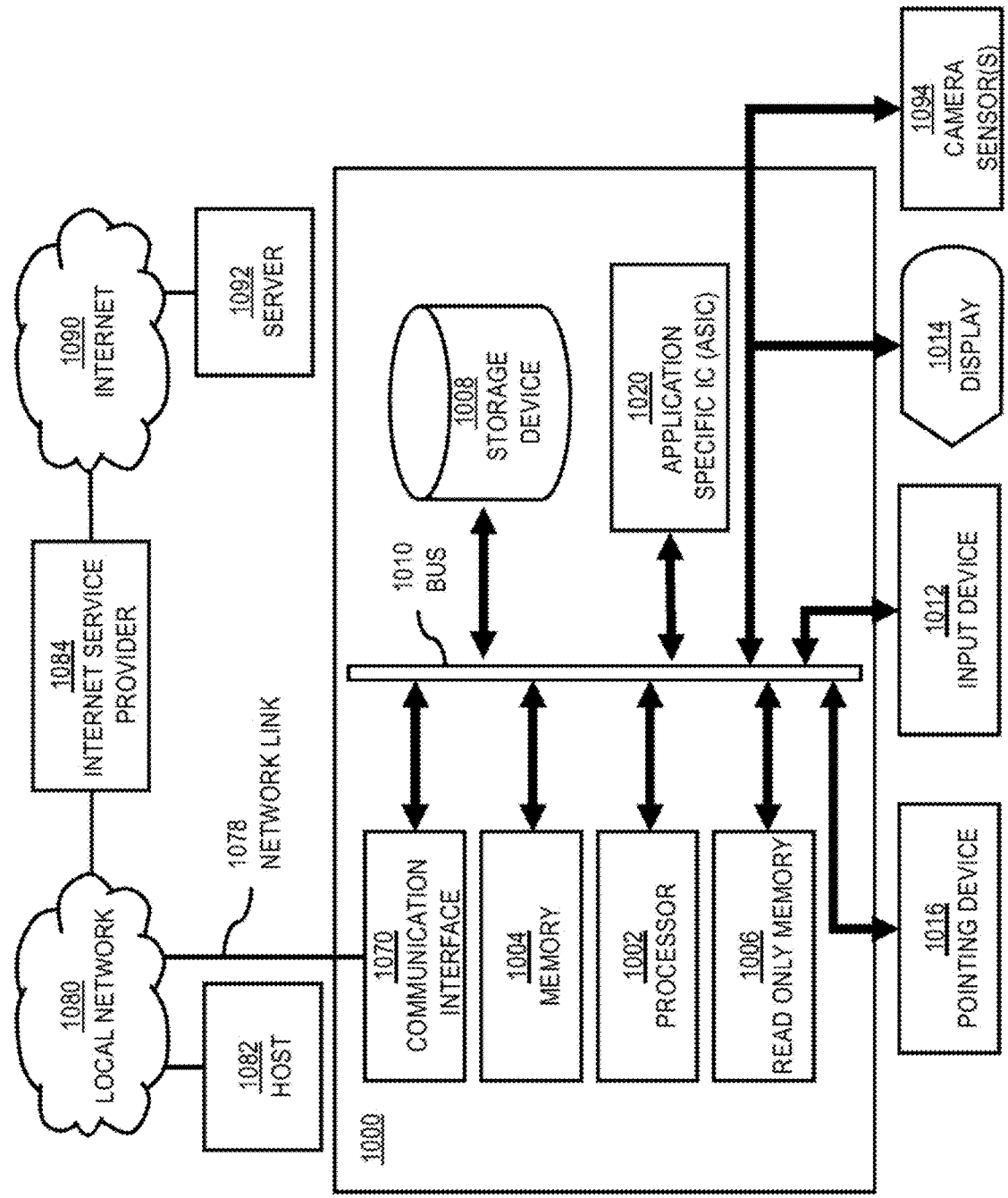
FIG. 10 is a diagram of hardware that can be used to implement various example embodiments.

FIG. 10 illustrates a computer system 1000 upon which various embodiments of the invention may be implemented. Although computer system 1000 is depicted with respect to a particular device or equipment, it is contemplated that other devices or equipment (e.g., network elements, servers, etc.) within FIG. 10 can deploy the illustrated hardware and components of system 1000. Computer system 1000 is programmed (e.g., via computer program code or instructions) to provide a real-time feedback during a sports activity based, at least in part, on analysis of sensor information as described herein and includes a communication mechanism such as a bus 1010 for passing information between other internal and external components of the computer system 1000. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of providing real-time feedback during a sports activity based, at least in part, on analysis of sensor information.

A bus 1010 includes one or more parallel conductors of information so that information is transferred quickly among devices coupled to the bus 1010. One or more processors 1002 for processing information are coupled with the bus 1010.

A processor (or multiple processors) 1002 performs a set of operations on information as specified by computer program code related to providing real-time feedback during a sports activity based, at least in part, on analysis of sensor information. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1010 and placing information on the bus 1010. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1002, such as a sequence of operation codes, constitute processor instructions, also called computer system instructions or, simply, computer instructions. Processors may be implemented as mechanical, electrical, magnetic, optical, chemical, or quantum components, among others, alone or in combination.

Computer system 1000 also includes a memory 1004 coupled to bus 1010. The memory 1004, such as a random-access memory (RAM) or any other dynamic storage device, stores information including processor instructions for providing real-time feedback during a sports activity based, at least in part, on analysis of sensor information. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of processor instructions. The computer system 1000 also includes a read only memory (ROM) 1006 or any other static storage device coupled to the bus 1010 for storing static information, including instructions, that is not changed by the computer system 1000. Some memory is composed of volatile storage that loses the information stored thereon when power is lost. Also coupled to bus 1010 is a non-volatile (persistent) storage device 1008, such as a magnetic disk, optical disk or flash card, for storing information, including instructions, that persists even when the computer system 1000 is turned off or otherwise loses power.

Information, including instructions for providing a real-time feedback during a sports activity based, at least in part, on analysis of sensor information, is provided to the bus 1010 for use by the processor from an external input device 1012, such as a keyboard containing alphanumeric keys operated by a human user, a microphone, an Infrared (IR) remote control, a joystick, a game pad, a stylus pen, a touch screen, or a sensor. A sensor detects conditions in its vicinity and transforms those detections into physical expression compatible with the measurable phenomenon used to represent information in computer system 1000. Other external devices coupled to bus 1010, used primarily for interacting with humans, include a display device 1014, such as a vacuum fluorescent display (VFD), a liquid crystal display (LCD), a light-emitting diode (LED), an organic light-emitting diode (OLED), a quantum dot display, a virtual reality (VR) headset, a plasma screen, a cathode ray tube (CRT), or a printer for presenting text or images, and a pointing device 1016, such as a mouse, a trackball, cursor direction keys, or a motion sensor, for controlling a position of a small cursor image presented on the display 1014 and issuing commands associated with graphical elements presented on the display 1014, and one or more camera sensors 1094 for capturing, recording and causing to store one or more still and/or moving images (e.g., videos, movies, etc.) which also may comprise audio recordings. In some embodiments, for example, in embodiments in which the computer system 1000 performs all functions automatically without human input, one or more of external input device 1012, a display device 1014 and pointing device 1016 may be omitted.

In the illustrated embodiment, special purpose hardware, such as an application specific integrated circuit (ASIC) 1020, is coupled to bus 1010. The special purpose hardware is configured to perform operations not performed by processor 1002 quickly enough for special purposes. Examples of ASICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a one-way or two-way communication coupling to a variety of external devices that operate with their own processors, such as printers, scanners, and external disks. In general, the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. For wireless links, the communications interface 1070 sends or receives or both sends and receives electrical, acoustic or electromagnetic signals, including infrared and optical signals, that carry information streams, such as digital data. For example, in wireless handheld devices, such as mobile telephones like cell phones, the communications interface 1070 includes a radio band electromagnetic transmitter and receiver called a radio transceiver. In certain embodiments, the communications interface 1070 enables connection to the communication network 107 for providing real-time feedback during a sports activity based, at least in part, on analysis of sensor information to the UE 101.

The term "computer-readable medium" as used herein refers to any medium that participates in providing information to processor 1002, including instructions for execution. Such a medium may take many forms, including, but not limited to a computer-readable storage medium (e.g., non-volatile media, volatile media), and transmission media. Non-transitory media, such as non-volatile media, include, for example, optical or magnetic disks, such as storage device 1008. Volatile media include, for example, dynamic memory 1004. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1020.

Network link 1078 typically provides information communication using transmission media through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090.

A computer called a server host 1092 connected to the Internet hosts a process that provides a service in response to information received over the Internet. For example, server host 1092 hosts a process that provides information representing video data for presentation at display 1014. It is contemplated that the components of system 1000 can be deployed in various configurations within other computer systems, e.g., host 1082 and server 1092.

At least some embodiments of the invention are related to the use of computer system 1000 for implementing some or all of the techniques described herein. According to one embodiment of the invention, those techniques are performed by computer system 1000 in response to processor 1002 executing one or more sequences of one or more processor instructions contained in memory 1004. Such instructions, also called computer instructions, software and program code, may be read into memory 1004 from another computer-readable medium such as storage device 1008 or network link 1078. Execution of the sequences of instructions contained in memory 1004 causes processor 1002 to perform one or more of the method steps described herein. In alternative embodiments, hardware, such as ASIC 1020, may be used in place of or in combination with software to implement the invention. Thus, embodiments of the invention are not limited to any specific combination of hardware and software, unless otherwise explicitly stated herein.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server host 1092 transmits program code for a particular application, requested by a message sent from computer 1000, through Internet 1090, ISP equipment 1084, local network 1080 and communications interface 1070. The received code may be executed by processor 1002 as it is received, or may be stored in memory 1004 or in storage device 1008 or any other non-volatile storage for later execution, or both. In this manner, computer system 1000 may obtain application program code in the form of signals on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

FIG. 11 illustrates a chip set or chip 1100 upon which various embodiments of the invention may be implemented. Chip set 1100 is programmed to provide real-time feedback during a sports activity based, at least in part, on analysis of sensor information as described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 1100 can be implemented in a single chip. It is further contemplated that in certain embodiments the chip set or chip 1100 can be implemented as a single "system on a chip." It is further contemplated that in certain embodiments a separate ASIC would not be used, for example, and that all relevant functions as disclosed herein would be performed by a processor or processors. Chip set or chip 1100, or a portion thereof, constitutes a means for performing one or more steps of providing user interface navigation information associated with the availability of functions. Chip set or chip 1100, or a portion thereof, constitutes a means for performing one or more steps of providing real-time feedback during a sports activity based, at least in part, on analysis of sensor information.

In one embodiment, the chip set or chip 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a more general purpose processor. Other specialized components to aid in performing the inventive functions described herein may include one or more field programmable gate arrays (FPGA), one or more controllers, or one or more other special-purpose computer chips.

In one embodiment, the chip set or chip 1100 includes merely one or more processors and some software and/or firmware supporting and/or relating to and/or for the one or more processors.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform the inventive steps described herein to provide a real-time feedback during a sports activity based, at least in part, on analysis of sensor information. The memory 1105 also stores the data associated with or generated by the execution of the inventive steps.

FIG. 12 is a diagram of exemplary components of a mobile terminal (e.g., handset) for communications, which is capable of operating in the system of FIG. 1, according to one embodiment. In some embodiments, mobile terminal 1201, or a portion thereof, constitutes a means for performing one or more steps of providing real-time feedback during a sports activity based, at least in part, on analysis of sensor information. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1203, a Digital Signal Processor (DSP) 1205, and a receiver/transmitter unit including a microphone gain control unit and a speaker gain control unit. A main display unit 1207 provides a display to the user in support of various applications and mobile terminal functions that perform or support the steps of providing real-time feedback during a sports activity based, at least in part, on analysis of sensor information. The display 1207 includes display circuitry configured to display at least a portion of a user interface of the mobile terminal (e.g., mobile telephone). Additionally, the display 1207 and display circuitry are configured to facilitate user control of at least some functions of the mobile terminal. An audio function circuitry 1209 includes a microphone 1211 and microphone amplifier that amplifies the speech signal output from the microphone 1211. The amplified speech signal output from the microphone 1211 is fed to a coder/decoder (CODEC) 1213.

A radio section 1215 amplifies the power and converts frequency in order to communicate with a base station, which is included in a mobile communication system, via antenna 1217. The power amplifier (PA) 1219 and the transmitter/modulation circuitry are operationally responsive to the MCU 1203, with an output from the PA 1219 coupled to the duplexer 1221 or circulator or antenna switch, as known in the art. The PA 1219 also couples to a battery interface and power control unit 1220.

In use, a user of mobile terminal 1201 speaks into the microphone 1211 and his or her voice along with any detected background noise is converted into an analog voltage. The analog voltage is then converted into a digital signal through the Analog to Digital Converter (ADC) 1223. The control unit 1203 routes the digital signal into the DSP 1205 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1225 for compensation of any frequency-dependent impairments that occur during transmission though the air such as phase and amplitude distortion. After equalizing the bit stream, the modulator 1227 combines the signal with an RF signal generated in the RF interface 1229. The modulator 1227 generates a sine wave by way of frequency or phase modulation. In order to prepare the signal for transmission, an up-converter 1231 combines the sine wave output from the modulator 1227 with another sine wave generated by a synthesizer 1233 to achieve the desired frequency of transmission. The signal is then sent through a PA 1219 to increase the signal to an appropriate power level. In practical systems, the PA 1219 acts as a variable gain amplifier whose gain is controlled by the DSP 1205 from information received from a network base station. The signal is then filtered within the duplexer 1221 and optionally sent to an antenna coupler 1235 to match impedances to provide maximum power transfer. Finally, the signal is transmitted via antenna 1217 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1201 are received via antenna 1217 and immediately amplified by a low noise amplifier (LNA) 1237. A down-converter 1239 lowers the carrier frequency while the demodulator 1241 strips away the RF leaving only a digital bit stream. The signal then goes through the equalizer 1225 and is processed by the DSP 1205. A Digital to Analog Converter (DAC) 1243 converts the signal and the resulting output is transmitted to the user through the speaker 1245, all under control of a Main Control Unit (MCU) 1203 which can be implemented as a Central Processing Unit (CPU).

The MCU 1203 receives various signals including input signals from the keyboard 1247. The keyboard 1247 and/or the MCU 1203 in combination with other user input components (e.g., the microphone 1211) comprise a user interface circuitry for managing user input. The MCU 1203 runs a user interface software to facilitate user control of at least some functions of the mobile terminal 1201 to provide real-time feedback during a sports activity based, at least in part, on analysis of sensor information. The MCU 1203 also delivers a display command and a switch command to the display 1207 and to the speech output switching controller, respectively. Further, the MCU 1203 exchanges information with the DSP 1205 and can access an optionally incorporated SIM card 1249 and a memory 1251. In addition, the MCU 1203 executes various control functions required of the terminal. The DSP 1205 may, depending upon the implementation, perform any of a variety of conventional digital processing functions on the voice signals. Additionally, DSP 1205 determines the background noise level of the local environment from the signals detected by microphone 1211 and sets the gain of microphone 1211 to a level selected to compensate for the natural tendency of the user of the mobile terminal 1201.

The CODEC 1213 includes the ADC 1223 and DAC 1243. The memory 1251 stores various data including call incoming tone data and is capable of storing other data including music data received via, e.g., the global Internet. The software module could reside in RAM memory, flash memory, registers, or any other form of writable storage medium known in the art. The memory device 1251 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1249 carries, for instance, important information, such as the cellular phone number, the carrier supplying service, subscription details, and security information. The SIM card 1249 serves primarily to identify the mobile terminal 1201 on a radio network. The card 1249 also contains a memory for storing a personal telephone number registry, text messages, and user specific mobile terminal settings.

Further, one or more camera sensors 1253 may be incorporated onto the mobile station 1201 wherein the one or more camera sensors may be placed at one or more locations on the mobile station. Generally, the camera sensors may be utilized to capture, record, and cause to store one or more still and/or moving images (e.g., videos, movies, etc.) which also may comprise audio recordings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising:
    receiving sensor data associated with one or more sensors arranged to track playing technique information of a player engaged in a sports activity;
    capturing, via an augmented reality display device, a field-of-view of the player during the sports activity;
    transmitting, in real-time, the captured field-of-view to another augmented reality display device associated with other players engaged in the sports activity;
    determining, via the augmented reality display device, a point-of-view (POV) of the player is obstructed during the sports activity;
    switching, in real-time, the obstructed POV of the player with an unobstructed POV of the other players engaged in the sports activity;
    processing the sensor data in real-time to determine the playing technique information;
    retrieving baseline information for the player;
    comparing the playing technique information with the baseline information;
    generating, in real-time with the engagement of the sports activity, an instructional message to modify playing technique of the player based on the comparison; and
    initiating presentation, during the sports activity, of the instructional message to a user interface of a device accessible by the player.

2. The method of claim 1, wherein the baseline information includes historical playing technique information of the player or target playing technique information, and wherein the target playing technique information is associated with another player, the method further comprising:
    receiving user input via the user interface to specify inclusion of the historical playing technique information or the target playing technique information; and
    configuring the baseline information based on the user input.

3. The method of claim 1, further comprising:
    determining degree of specificity of instructions relating to the modification of the playing technique; and
    filtering the sensor data according to the determined degree of specificity, wherein the generation of the instructional message is based on the filtered sensor data.

4. The method of claim 1, further comprising:
receiving user profile information for the player; and
generating an avatar of the player based on the user profile information, wherein the avatar is associated with the playing technique information.

5. The method of claim 1, wherein the sports activity is golfing, the method further comprising:
initiating transmission, in real-time, the playing technique information of the player to a second device accessible by a coach,
wherein the instructional message includes feedback by the coach.

6. The method of claim 1, wherein the instructional message is provided as auditory feedback to the player engaged in the sports activity.

7. The method of claim 1, wherein the one or more sensors are embedded or attached to apparatuses, apparels, wrist bands, or a combination thereof of the player to track the playing technique.

8. A method comprising:
receiving, a first input via a user interface of a device, wherein the first input specifies a play mode or a lesson mode;
receiving, a second input via the user interface of the device, wherein the second input specifies a degree of instructions, and wherein the specified degree of instructions relates to a modification of a playing technique during a sports activity;
capturing, via an augmented reality display device, a field-of-view of the player during the sports activity;
transmitting, in real-time, the captured field-of-view to another augmented reality display device associated with other players engaged in the sports activity;
determining, via the augmented reality display device, a point-of-view (POV) of the player is obstructed during the sports activity;
switching, in real-time, the obstructed POV of the player with an unobstructed POV of the other players engaged in the sports activity;
filtering sensor data according to the specified degree of instructions;
transmitting the filtered sensor data, the first input, and the second input; and
receiving an instructional message based on the filtered sensor data, the first input, and the second input.

9. The method of claim 8, further comprising:
receiving, a third input via the user interface of the device, wherein the third input specifies a profile of the player, and wherein the profile comprises a novice player, an intermediate player, or an expert player.

10. The method of claim 8, further comprising:
initiating presentation, during the sports activity, of the instructional message to the user interface of the device accessible by a player.

11. A system comprising:
one or more computing devices configured to perform,
receiving sensor data associated with one or more sensors arranged to track playing technique information of a player engaged in a sports activity;
capturing, via an augmented reality display device, a field-of-view of the player during the sports activity;
transmitting, in real-time, the captured field-of-view to another augmented reality display device associated with other players engaged in the sports activity;
determining, via the augmented reality display device, a point-of-view (POV) of the player is obstructed during the sports activity;
switching, in real-time, the obstructed POV of the player with an unobstructed POV of the other players engaged in the sports activity;
processing the sensor data in real-time to determine the playing technique information;
retrieving baseline information for the player;
comparing the playing technique information with the baseline information;
generating, in real-time with the engagement of the sports activity, an instructional message to modify playing technique of the player based on the comparison; and
initiating presentation, during the sports activity, of the instructional message to a user interface of a device accessible by the player.

12. The system of claim 11, wherein the baseline information includes historical playing technique information of the player or target playing technique information, and wherein the target playing technique information is associated with another player, the one or more computing devices being further configured to perform:
receiving user input via the user interface to specify inclusion of the historical playing technique information or the target playing technique information; and
configuring the baseline information based on the user input.

13. The system of claim 11, wherein the one or more computing devices are further configured to perform:
determining degree of specificity of instructions relating to the modification of the playing technique; and
filtering the sensor data according to the determined degree of specificity,
wherein the generation of the instructional message is based on the filtered sensor data.

14. The system of claim 11, wherein the one or more computing devices are further configured to perform:
receiving user profile information for the player; and
generating an avatar of the player based on the user profile information, wherein the avatar is associated with the playing technique information.

15. The system of claim 11, wherein the sports activity is golfing, the one or more computing devices being further configured to perform:
initiating transmission, in real-time, the playing technique information of the player to a second device accessible by a coach,
wherein the instructional message includes feedback by the coach.

16. The system of claim 11, wherein the instructional message is provided as auditory feedback to the player engaged in the sports activity.

17. The system of claim 11, wherein the one or more sensors are embedded or attached to apparatuses, apparels, wrist bands, or a combination thereof of the player to track the playing technique.

18. The system of claim 11, wherein the one or more computing devices are further configured to perform:
generating a periodic report regarding the playing technique of the player during the sports activity; and
determining a progress of the player based on the periodic reports, wherein a degree of specificity of instructions is based on the periodic reports.

* * * * *